United States Patent
Pei et al.

(10) Patent No.: US 7,941,217 B1
(45) Date of Patent: May 10, 2011

(54) TECHNIQUES FOR PROMOTING BIVENTRICULAR SYNCHRONY AND STIMULATION DEVICE EFFICIENCY USING INTENTIONAL FUSION

(75) Inventors: Xing Pei, Thousand Oaks, CA (US); Paul Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 449 days.

(21) Appl. No.: 12/055,166

(22) Filed: Mar. 25, 2008

(51) Int. Cl.
*A61N 1/00* (2006.01)
(52) U.S. Cl. ................ 607/9; 607/11; 607/25; 607/115
(58) Field of Classification Search ................ 607/9, 11, 607/25, 115
See application file for complete search history.

(56) References Cited

U.S. PATENT DOCUMENTS

| | | |
|---|---|---|
| 4,712,555 A | 12/1987 | Thornander et al. |
| 4,788,980 A | 12/1988 | Mann et al. |
| 4,928,688 A | 5/1990 | Mower |
| 4,940,052 A | 7/1990 | Mann et al. |
| 4,944,298 A | 7/1990 | Sholder |
| 5,086,774 A | 2/1992 | Duncan |
| 5,174,289 A | 12/1992 | Cohen |
| 5,179,949 A | 1/1993 | Chirife |
| 5,391,189 A | 2/1995 | Van Krieken et al. |
| 5,466,254 A | 11/1995 | Helland |
| 5,476,483 A | 12/1995 | Bornzin et al. |
| 5,643,327 A | 7/1997 | Dawson et al. |
| 5,741,308 A | 4/1998 | Sholder |
| 5,749,906 A | 5/1998 | Kieval et al. |
| 5,800,465 A | 9/1998 | Thompson et al. |
| 5,814,077 A | 9/1998 | Sholder et al. |
| 5,814,089 A | 9/1998 | Stokes et al. |
| 5,873,895 A | 2/1999 | Sholder et al. |
| 6,122,546 A | 9/2000 | Sholder et al. |
| 6,141,588 A | 10/2000 | Cox et al. |
| 6,144,880 A | 11/2000 | Ding et al. |
| 6,149,595 A * | 11/2000 | Seitz et al. ............ 600/438 |
| 6,285,907 B1 | 9/2001 | Kramer et al. |
| 6,314,323 B1 | 11/2001 | Ekwall |
| 6,360,127 B1 | 3/2002 | Ding et al. |
| 6,411,848 B2 | 6/2002 | Kramer et al. |
| 6,424,865 B1 | 7/2002 | Ding et al. |
| 6,473,645 B1 | 10/2002 | Levine |
| 6,473,647 B1 | 10/2002 | Bradley |
| 6,567,700 B1 | 5/2003 | Turcott et al. |
| 6,596,730 B1 | 7/2003 | Coulton et al. |

(Continued)

FOREIGN PATENT DOCUMENTS

EP 0494487 B1 1/1996

(Continued)

OTHER PUBLICATIONS

Erich Ebner et al., "Ventricular Evoked Response as Clinical Marker for Hemodynamic Changes in Dilative Cardiomyopathy," PACE, Feb. 2004; vol. 27, pp. 166-174.

(Continued)

*Primary Examiner* — Niketa I Patel
*Assistant Examiner* — Nicole F Lavert

(57) ABSTRACT

An exemplary method includes providing an optimal interventricular interval, determining an atrio-ventricular conduction delay for the ventricle having faster atrio-ventricular conduction, determining an interventricular conduction delay and determining an advance atrio-ventricular pacing interval, for use in pacing the ventricle having slower atrio-ventricular conduction, based at least in part on the optimal interventricular interval and the interventricular conduction delay. Other exemplary methods, devices, systems, etc., are also disclosed.

18 Claims, 14 Drawing Sheets

U.S. PATENT DOCUMENTS

| | | |
|---|---|---|
| 6,606,516 B2 | 8/2003 | Levine |
| 6,622,040 B2 | 9/2003 | Ding et al. |
| 6,669,194 B2 | 12/2003 | VanHout |
| 6,711,439 B1 | 3/2004 | Bradley et al. |
| 6,751,503 B1 | 6/2004 | Kroll |
| 6,754,530 B2 | 6/2004 | Bakels et al. |
| 6,804,555 B2 | 10/2004 | Warkentin |
| 6,934,586 B2 | 8/2005 | Struble et al. |
| 6,959,214 B2 | 10/2005 | Pape et al. |
| 7,203,541 B2 | 4/2007 | Sowelam et al. |
| 7,248,925 B2 | 7/2007 | Bruhns et al. |
| 2001/0016759 A1 | 8/2001 | Kramer et al. |
| 2001/0031993 A1 | 10/2001 | Salo et al. |
| 2002/0049478 A1 | 4/2002 | Ding et al. |
| 2002/0062139 A1 | 5/2002 | Ding |
| 2002/0077559 A1 | 6/2002 | Ding et al. |
| 2002/0161410 A1 | 10/2002 | Kramer et al. |
| 2003/0004548 A1 | 1/2003 | Warkentin |
| 2003/0014084 A1 | 1/2003 | Van Hout |
| 2003/0060851 A1 | 3/2003 | Kramer et al. |
| 2003/0130702 A1 | 7/2003 | Kramer et al. |
| 2003/0195580 A1 | 10/2003 | Bradley et al. |
| 2003/0204212 A1 | 10/2003 | Burnes et al. |
| 2004/0133246 A1 | 7/2004 | Ding et al. |
| 2004/0147966 A1 | 7/2004 | Ding et al. |
| 2004/0158293 A1 | 8/2004 | Yonce et al. |
| 2004/0193223 A1 | 9/2004 | Kramer et al. |
| 2004/0220635 A1 | 11/2004 | Burnes |
| 2005/0090870 A1 | 4/2005 | Hine et al. |
| 2005/0149138 A1 | 7/2005 | Min et al. |
| 2006/0224198 A1* | 10/2006 | Dong et al. .................. 607/9 |
| 2006/0276684 A1 | 12/2006 | Min et al. |

FOREIGN PATENT DOCUMENTS

| | | |
|---|---|---|
| EP | 1199085 A2 | 4/2002 |
| EP | 1234597 A2 | 8/2002 |
| WO | WO99/58191 | 11/1999 |
| WO | WO02051495 A2 | 7/2002 |
| WO | WO03/037427 A1 | 5/2003 |
| WO | WO2005/039690 A1 | 5/2005 |

OTHER PUBLICATIONS

Thomas C. Gerber, MD et al., "Left Ventricular and Biventricular Pacing in Congestive Heart Failure," Mayo Clinic Proc., Aug. 2001; vol. 76, pp. 803-812.

Jose L. Merino, MD et al., "Bundle-Branch Reentry and the Postpacing Interval After Entrainment by Right Ventricular Apex Stimulation—A New Approach to Elucidate the Mechanism of Wide-QRS-Complex Tachycardia with Atrioventricular Dissociation," Circulation, Feb. 2001; vol. 103, pp. 1102-1108.

Gregory S. Nelson, PhD et al., "Left Ventricular or Biventricular Pacing Improves Cardiac Function at Diminished Energy Cost in Patients with Dilated Cardiomyopathy and Left Bundle-Branch Block," Circulation, Dec. 2000; vol. 102, pp. 3053-3059.

G. Schreier et al., "Correlation Between Changes in Stroke Volume and the Paced Intracardiac Electrogram," Europace, Jul. 2002; vol. 4, pp. 303-310.

Andreas Schuchert et al., "Effects of Body Position and Exercise on Evoked Response Signal for Automatic Threshold Activation," PACE, Oct. 1999; vol. 22, pp. 1476-1480.

Paul Wang et al., "Timing Cycles for Biventricular Pacing", PACE, Jan. 2002; vol. 25, No. 1, pp. 62-75.

R. Chirife et al., "Nonphysiological Left Heart AV Intervals as a Result of DDD and AAI "Physiological"Pacing ", PACE, Nov. 1991; vol. 14, Part II, pp. 1752-1756.

Raul Chirife, "Proposal of a Method for Automatic Optimization of Left Heart Atrioventricular Interval Applicable to DDD Pacemakers", PACE, Jan. 1995; vol. 18, Part 1, pp. 49-56.

Raul Chirife, M.D., Letters to the Editor, PACE, May 2000; vol. 23, pp. 926.

Toshiyuki Ishikawa et al., "Prediction of Optimal Atrioventricular Delay in Patients with Implanted DDD Pacemakers", PACE, Sep. 1999; vol. 22, pp. 1365-1371.

Raúl Chirife et al., "Automatic Beat-To-Beat Left Heart AV Normalization: Is it Possible?", PACE, Nov. 2003; vol. 26, pp. 2103-2110.

Ismer, B. et al, "Impact of Discriminating Electrophysiological and Electromechanical Determinants of the Optimal AV Delay in Right and Biventricular DDD Pacing," Folia Cardiol. 2006, tom 13, supl. C.

Levine, Paul A. MD, FACC "Role of the AV Interval in DDD Pacing: Insights into Programming".

Levine, Paul A. MD, FACC, "Clinical Distribution, Ventricular Activation Sequence and Hemodynamics-3".

Chamorro et al., An Even More Physiological Pacing: Changing the Sequence of Ventricular Activation.

Levine, Paul A. MD, FACC, "Optimizing AV Delay in CRT Systems at Implant based on IACT".

NonFinal Office Action, mailed Nov. 17, 2005: Related U.S. Appl. No. 10/703,070.

Final Office Action, mailed Jul. 31, 2006: Related U.S. Appl. No. 10/703,070.

Advisory Action, mailed Oct. 20, 2006: Related U.S. Appl. No. 10/703,070.

NonFinal Office Action, mailed Apr. 10, 2007: Related U.S. Appl. No. 10/703,070.

NonFinal Office Action, mailed Apr. 10, 2007: Related U.S. Appl. No. 10/974,123.

NonFinal Office Action, mailed Apr. 17, 2008: Related U.S. Appl. No. 10/974,123.

NonFinal Office Action, mailed Jul. 31, 2006: Related U.S. Appl. No. 10/986,273.

Final Office Action, mailed Jul. 16, 2007: Related U.S. Appl. No. 10/986,273.

Final Office Action, mailed Mar. 14, 2008: Related U.S. Appl. No. 10/986,273.

NonFinal Office Action, mailed Oct. 9, 2007: Related U.S. Appl. No. 10/980,140.

NonFinal Office Action, mailed Jun. 5, 2008: Related U.S. Appl. No. 11/255,332.

* cited by examiner

INTERVENTRICULAR CONDUCTION 400

PIVCD-RL = $R_{LV} - V_{RV}$ $\Delta_{PIVCD}$ = $(R_{RV} - V_{LV}) - (R_{LV} - V_{RV})$    $\Delta_{PIVCD}$ = PIVCD-LR - PIVCD-RL Exemplary Scenario 800
(CRT with a Single Lead by Fusion with the Already present RBBB)

Instrinsic (Lead II)
804

RV Paced
808

Intentional Fusion
812

Exemplary Methods 1400

States 1410

$AS_0$ = Base State (e.g., Rest)
$AS_1$ = Active State 1
$AS_2$ = Active State 2
$AS_N$ = Active State N

PV or AV States 1420

$\beta = \delta/DD(AS_0)$
$\beta = \delta/AD(AS_0)$ $\delta = f(\Delta P(AS_0))$   $\delta = f(\Delta A(AS_0))$
$\delta = f(\Delta P(AS_x))$   $\delta = f(\Delta A(AS_x))$ $PV(AS_0) = \Delta P(AS_0) + \delta$
$AV(AS_0) = \Delta A(AS_0) + \delta$ $PV(AS_x) = \Delta P(AS_x) + \beta*DD(AS_x)$
$AV(AS_x) = \Delta A(AS_x) + \beta*AD(AS_x)$ $PV(AS_0) = \Delta P(AS_0) + \delta - PL$
$AV(AS_0) = \Delta A(AS_0) + \delta - PL$ $PV(AS_x) = \Delta P(AS_x) + \beta*DD(AS_x) - PL$
$AV(AS_x) = \Delta A(AS_x) + \beta*AD(AS_x) - PL$

VV States 1430

$\alpha$ = Constant
$\alpha = \alpha(AS_0)$
$\alpha = \alpha(AS_x)$ $\Delta(AS_0) = R_{LV}(AS_0) - R_{RV}(AS_0)$
$\Delta(AS_x) = R_{LV}(AS_x) - R_{RV}(AS_x)$ $\Delta_{IVCD}(AS_0) = IVCD\text{-}LR(AS_0) - IVCD\text{-}RL(AS_0)$
$\Delta_{IVCD}(AS_x) = IVCD\text{-}LR(AS_x) - IVCD\text{-}RL(AS_x)$ $VV(AS_0) = \alpha*(\Delta(AS_0) + \Delta_{IVCD}(AS_0))$
$VV(AS_x) = \alpha*(\Delta(AS_x) + \Delta_{IVCD}(AS_x))$ $VV(AS_0) = \alpha*(\Delta(AS_0) + \Delta_{IVCD}(AS_0)) - \Delta PL$
$VV(AS_x) = \alpha*(\Delta(AS_x) + \Delta_{IVCD}(AS_x)) - \Delta PL$

Fig. 14

TECHNIQUES FOR PROMOTING BIVENTRICULAR SYNCHRONY AND STIMULATION DEVICE EFFICIENCY USING INTENTIONAL FUSION

RELATED APPLICATIONS

This application is related to U.S. patent application Ser. No. 10/703,070, filed Nov. 5, 2003, entitled "Method for Ventricular Pacing," which has been expired as of Sep. 29, 2008, and to U.S. patent application Ser. No. 10/980,140, filed Nov. 1, 2004, entitled "Methods for Ventricular Pacing Using Interference," which has been expired as of Jun. 9, 2009.

TECHNICAL FIELD

Subject matter presented herein generally relates to cardiac pacing therapy and, in particular, to optimizing ventricular pacing.

BACKGROUND

Clinical studies related to cardiac pacing have shown that an optimal atrio-ventricular delay (e.g., AV delay) and/or an optimal interventricular delay (e.g., VV delay) can improve cardiac performance. For example, given an optimal VV delay, cardiac resynchronization therapy (CRT) can deliver electrical stimulation to the heart at a right ventricular site (e.g., apex or interventricular septum) and then deliver electrical stimulation to the heart at a left ventricular site (e.g., postero-lateral wall) to improve mechanical dyssynchrony associated with an intrinsic abnormal ventricular activation pattern (e.g., due to left bundle branch block). With respect to AV delay, simply setting a CRT device's AV delay to a value less than a patient's intrinsic conduction time (i.e., to reduce competition from intrinsic activity with delivered electrical stimuli to the ventricles) is not necessarily optimal as results from the DAVID trial indicate that an excessively short AV delay can cause potentially detrimental, unnecessary ventricular pacing. Similarly, an overly long AV delay can be as counterproductive as an overly short AV delay for patients with intact nodal AV condition. Indeed, a truly optimal AV delay may cause CRT to deliver optimal intermittent ventricular pacing (i.e., an AV delay that is not too short and not too long).

Optimization of an AV delay and/or a VV delay often occurs at implantation. However, what is "optimal" for an AV delay and/or a VV delay depends on a variety of factors that may vary over time. Hence, sometimes, re-optimization of a delay or delays occurs during a follow-up consultation. While such optimizations are beneficial, the benefits may not be long lasting due to changes in various factors related to device condition, cardiac function, patient behavior, etc. Such factors may change unpredictably between consultations. Further, as the period between consultations increases, the chances that a patient's CRT is using suboptimal delays increases.

As described herein, various exemplary methods, devices, systems, etc., aim to determine and/or adjust AV delay, VV delay and/or other inter-chamber delays. Particular techniques involving such delays are presented for intentional fusion where one ventricle can be activated via an atrial to ventricular conducted depolarization and where the other ventricle is activated via artificially delivered electrical stimulation. Such techniques may use an optimal AV delay that is neither too short nor too long and that allows for intermittent ventricular pacing.

SUMMARY

An exemplary method includes providing an optimal interventricular interval, determining an atrio-ventricular conduction delay for the ventricle having faster atrio-ventricular conduction, determining an interventricular conduction delay and determining an advance atrio-ventricular pacing interval, for use in pacing the ventricle having slower atrio-ventricular conduction, based at least in part on the optimal interventricular interval and the interventricular conduction delay. Other exemplary methods, devices, systems, etc., are also disclosed. In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

FIG. 14 is a block diagram of various exemplary methods for adjusting one or more parameters with respect to patient activity state.

DETAILED DESCRIPTION

Overview

Exemplary methods, devices, systems, etc., described herein pertain generally to ventricular pacing. For example, various exemplary methods include deciding whether to use ventricular pacing and, if so, whether to pace in a single ventricle or in both ventricles. If such a method decides that ventricular pacing is appropriate, then the method may also determine an atrio-ventricular delay for one or both ventricles. For the case of bi-ventricular pacing, the method may determine an atrio-ventricular delay for each ventricle and/or an interventricular delay (e.g., which may be inherent in the use of two atrio-ventricular delay times). For the case where a single ventricle is paced, a method may determine values for one or more pacing parameters to cause intentional fusion. Such techniques may reduce frequency of ventricular or bi-ventricular pacing and/or enhance cardiac performance. Further, such techniques may optimize pacing as a function of time or in response to changes in any of a variety of factors related to cardiac and/or device performance.

The following description begins with a discussion of exemplary implantable devices and associated components followed by a discussion of heart rhythms and associated waveforms. Next, a discussion of cardiac performance follows, and the detailed description continues with a discussion of various exemplary methods, devices, systems, etc.

Exemplary Stimulation Device

The techniques described below are intended to be implemented in connection with any stimulation device that is configured or configurable to stimulate nerves and/or stimulate and/or shock a patient's heart.

Figure 1:
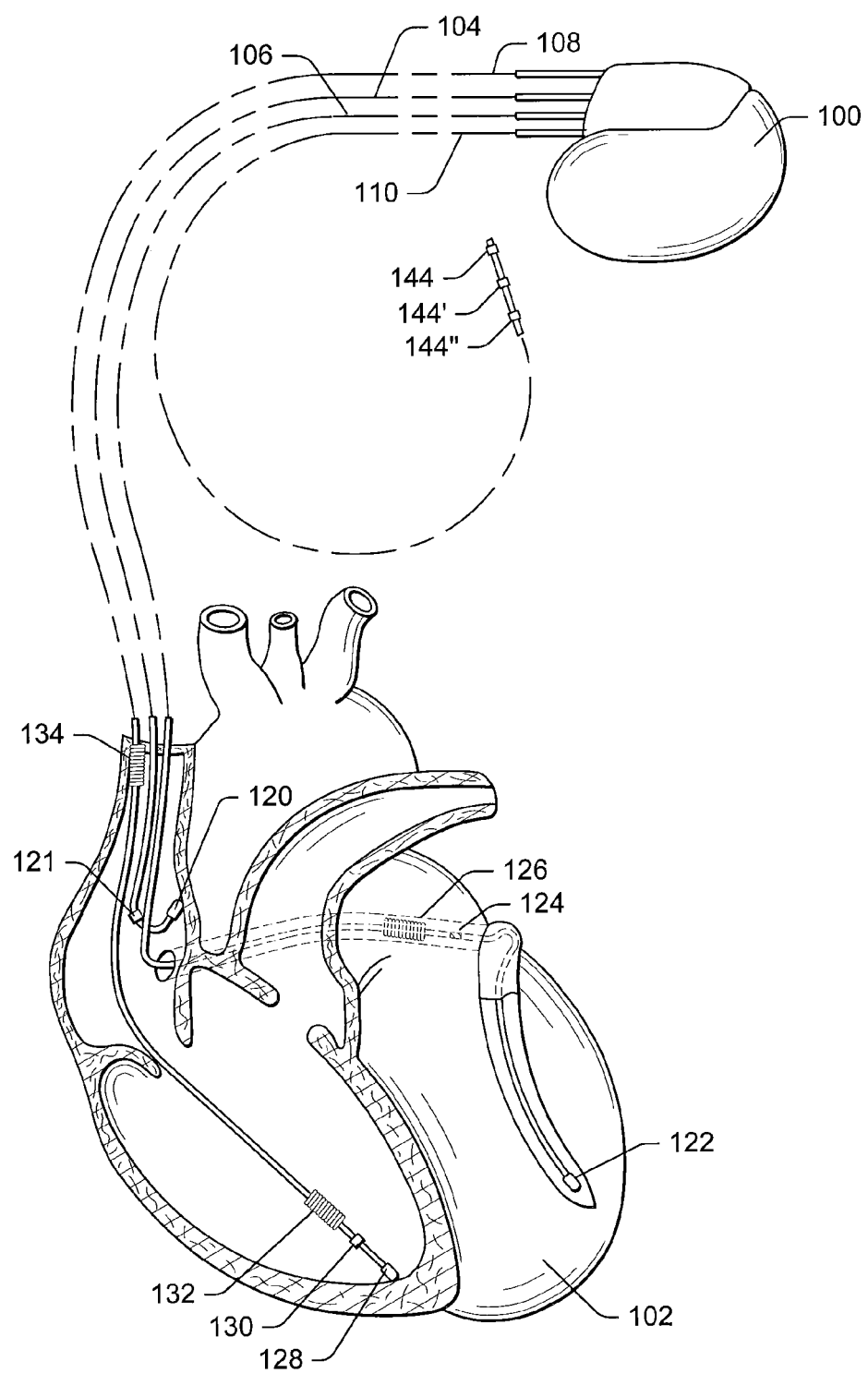
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation and/or sensing. Such a lead may be positioned epicardially for cardiac stimulation and/or sensing.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
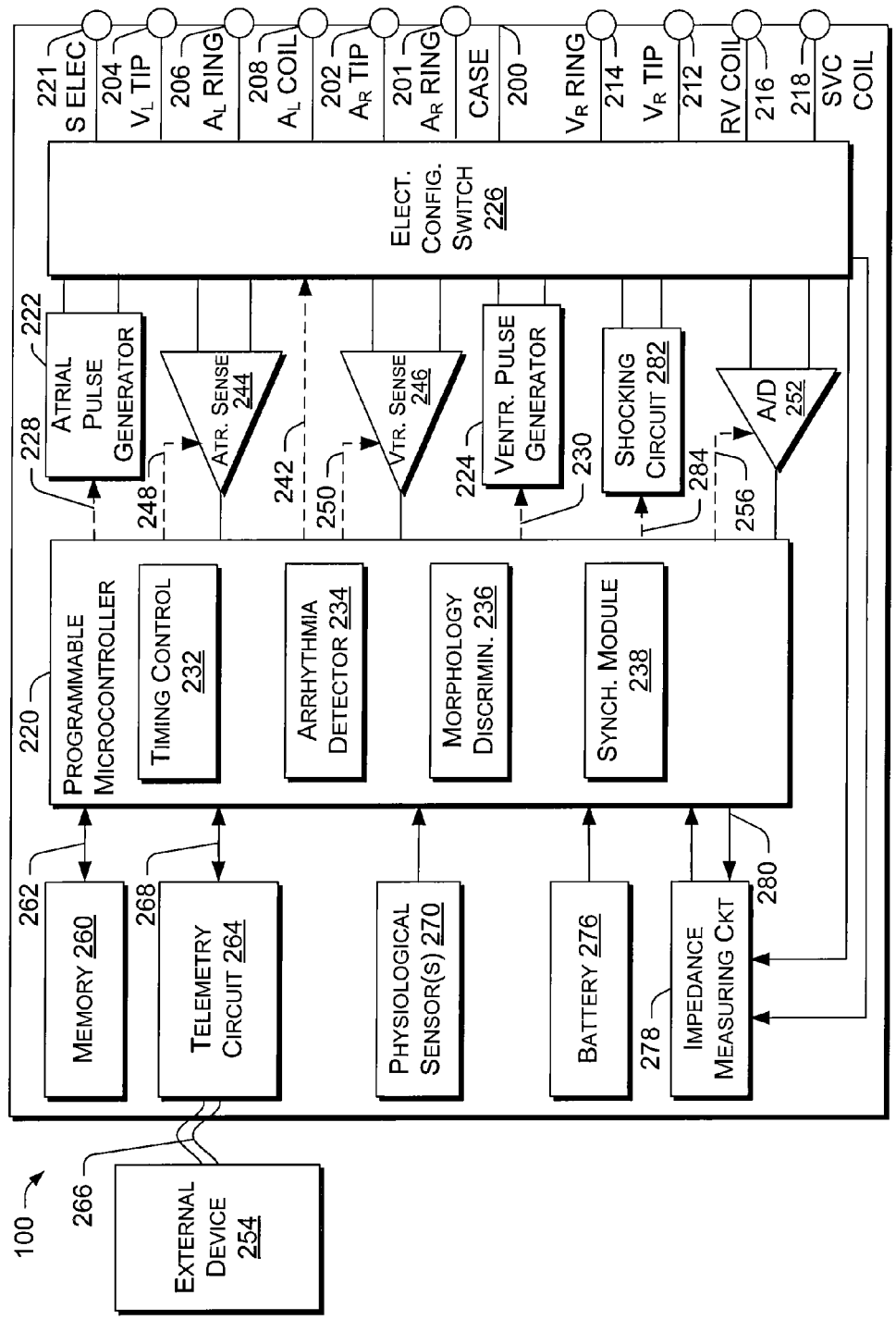
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. In instances where the device is configured to stimulate nerve or non-cardiac tissue (e.g., via lead 110), an electrode (e.g., 144, 144', 144") may be connected to the device via any suitable terminal (e.g., the terminal S ELEC 221 may provide for nerve stimulation).

To support right chamber sensing, pacing and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. In the example of FIG. 2, the microcontroller 220 includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 220 includes the ability to process or monitor input signals (data or information) as controlled by a program code stored in a designated block of memory. The type of microcontroller is not critical to the described implementations. Rather, any suitable microcontroller may be used that carries out the functions associated with one or more of the exemplary methods described herein.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a sensor module such as but not limited to minute ventilation (MV) response, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a synchronization module 238 for performing a variety of tasks related to ventricular synchrony. This component can be utilized by the stimulation device 100 for determining desirable times to administer various therapies, including, but not limited to, ventricular stimulation therapy, biventricular stimulation therapy, resynchronization therapy, atrial stimulation therapy, etc. The synchronization module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. Such a module may help make determinations as to interference or fusion, as described in more detail below.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture (e.g., for detecting evoked responses).

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. Automatic gain control can allow the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events can be classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Through appropriate switching, cardiac signals can be applied to inputs of an analog-to-digital (A/D) data acquisition system 252. In the example of FIG. 2, the data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the lead 110 through the switch 226 to sample signals across any pair of desired electrodes.

The microcontroller 220 is further coupled to a memory 260 by a suitable data/address bus 262, where the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, wave shape, number of pulses, and vector of each shocking pulse to be delivered to the patient's heart 102 within each respective tier of therapy. The device 100 can be configured to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include one or more physiological sensors 270. For example, the device 100 may include a sensor commonly referred to as a "rate-responsive" sensor for use in adjusting pacing stimulation rate according to the activity state of a patient. The one or more physiological sensors 270 may include a sensor to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), a sensor to detect changes in the physiological condition of the heart and/or a sensor to detect diurnal changes in activity (e.g., detecting sleep and wake states). Accordingly, the microcontroller 220 can respond to sensed information by adjusting one or more of the various pacing parameters (such as rate, AA delay, AV delay, VV delay, etc.).

While the aforementioned pressure sensor is configured for right ventricular pressure, pressure may be sensed in other chambers. For example, the device 100 may acquire information from a pressure sensor for left atrial pressure (see, e.g., U.S. Pat. No. 6,970,742, to Mann et al., "Method for detecting, diagnosing, and treating cardiovascular disease", issued Nov. 29, 2005, which discusses a sensor package deployed across the atrial septum to sense left atrial pressure). Increased pressure in the left atrium is a predictor of pulmonary congestion, which is the leading cause of hospitalization for congestive heart failure patients.

While shown as being included within the stimulation device 100, it is to be understood that the one or more of the one or more physiological sensors 270 may be external to the stimulation device 100, yet still be implanted within or carried by the patient. Examples of physiological sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483, entitled "System and method for modulating the base rate during sleep for a rate-responsive cardiac pacemaker", to Bornzin et al., issued Dec. 19, 1995, which patent is hereby incorporated by reference.

The one or more physiological sensors 270 may include a position sensor and/or a minute ventilation (MV) sensor to sense minute ventilation, which is defined as the total volume of air that moves in and out of a patient's lungs in a minute. Signals generated by such sensors can be passed to the microcontroller 220 for analysis for any of a variety of purposes (e.g., to determine whether to adjust the pacing rate, etc.). The microcontroller 220 can monitor signals from appropriate sensors for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
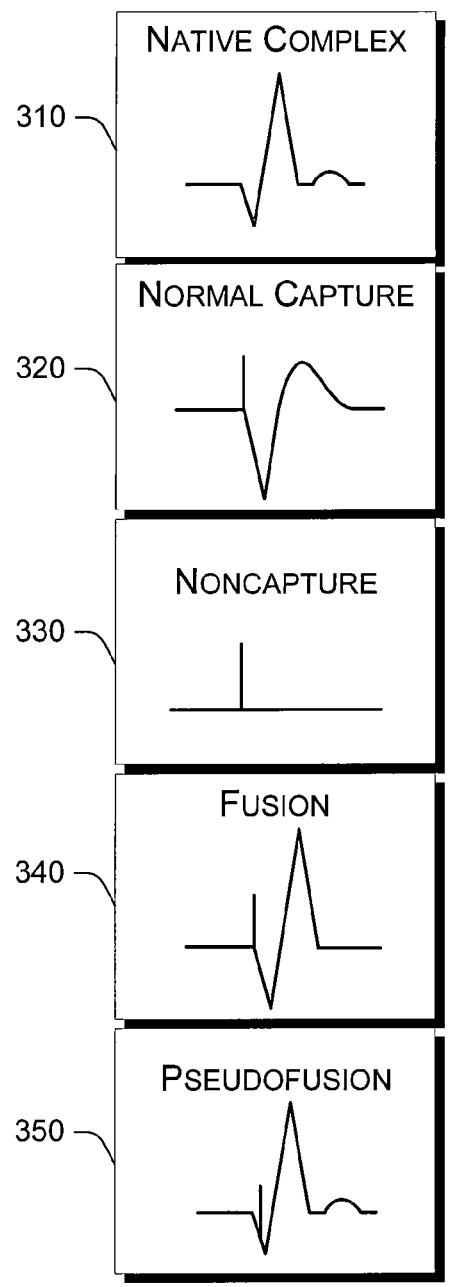
FIG. 3 is a series of waveforms related to native cardiac activity and cardiac activity responsive to artificial electrical stimulation.

Referring to FIG. 3, various exemplary waveforms 300 are shown. As discussed herein, a ventricular waveform caused by a ventricular stimulus (V) is generally referred to as an evoked response (ER) while a ventricular waveform caused by a native stimulus (e.g., conducted via the atrioventricular node or bundle (AVN)) is generally referred to as an R wave or native QRS complex. Another type of ventricular waveform discussed herein is caused by a stimulus in one ventricle traveling to the other ventricle and then causing depolarization of the other ventricle. Such a waveform is referred to as an $R_V$ wave, i.e., an R wave caused by ventricle to ventricle conduction, or referred to as a conducted evoked response ($ER_c$), i.e., an evoked response in one ventricle due to stimulation and depolarization of the other ventricle.

As described herein, and shown in Table 1, the terms primary(1°), secondary(2°) and tertiary(3°) simply refer to an order of events that help to define the symbols: P, A, R, $R_c$, $R_v$, V, ER and $ER_c$. For example, contraction of a ventricle (R) normally occurs after and in response to sinus activity (P); hence, the sinus activity (P) may be referred to as a primary event(1°) and contraction of the ventricle (R) may be referred to as a secondary event(2° caused by the primary event(1°). In this example, if the ventricle was paced (V) prior to conduction of the sinus activity (P), then contraction of the ventricle (ER) would be a primary event(1°).

For a patient with left bundle branch block (LBBB), sinus activity (P), a primary event(1°), causes depolarization of the right ventricle (R), a secondary event(2°), which then causes, by conduction, depolarization of the left ventricle ($R_c$), which may be referred to as a tertiary event(3°) of the sinus activity (P). Subscripts may be added to V, ER, R, $R_c$, RV, or $ER_c$ to denote association with the right ventricle (RV) or the left ventricle (LV).

The various events can be used to determine intervals. For example, a PR interval, a $PR_c$ interval, an $RR_c$ interval, an AV interval, a $V_{RV}$ interval, etc. Where ventricle designators are used, these examples may become for the right ventricle $PR_{RV}$, $PR_{C-RV}$, $R_{RV}R_{C-LV}$, $AV_{RV}$, $V_{RV}R_{V-LV}$, etc., and for the left ventricle $PR_{LV}$, $PR_{C-LV}$, $R_{LV}R_{C-RV}$, $AV_{LV}$, $V_{LV}R_{V-RV}$, etc.

TABLE 1

Classification of Activity

| Origin | Sinus | Paced | Other (e.g., PAC, PVC) |
|---|---|---|---|
| Right Atrium | 1° (P) | 1° (A) | 1° |
| Right Ventricle | 2° (R) | 1° (V, ER) | 1°, 2°, 3° |
|  | 3° ($R_c$) | 2° (R, $R_v$, $ER_c$) |  |
|  |  | 3° ($R_c$) |  |
| Left Ventricle | 2° (R) | 1° (V, ER) | 1°, 2°, 3° |
|  | 3° ($R_c$) | 2° (R, $R_v$, $ER_c$) |  |
|  |  | 3° ($R_c$) |  |

Referring to FIG. 3, the exemplary waveforms 300 include a native waveform 310 (e.g., per an ECG), which exhibits a distinct QRS complex and a distinct T wave. A paced ventricular waveform 320 that results in capture (i.e., an evoked response) differs from the native waveform 310. If the ventricles are refractory or if the stimulus energy is insufficient, then a non-capture waveform results 330. The particular non-capture waveform 330 corresponds to a scenario lacking native or intrinsic activity; the stylized waveform exhibits a stimulus artifact only. Of course, intracardiac electrograms (IEGMs) acquired with use of a blanking interval may not exhibit such an artifact.

Fusion is typically characterized by a wave complex formed by depolarization of the myocardium initiated by both a non-native stimulus and a native stimulus or two native pacemaker foci activating a given chamber at virtually the same time. As shown in FIG. 3, a fusion waveform 340 includes characteristics of a native waveform and a paced ventricular waveform. In particular, the waveform 340 includes depolarization due to an administered stimulus. In contrast, pseudofusion is typically characterized by a wave complex formed by depolarization of the myocardium initiated by a native activation; however, a non-native activation, that does not contribute to depolarization, is present that distorts the wave complex. The exemplary waveforms 300 include a pseudofusion waveform 350, which exhibits a native waveform and a stimulus artifact wherein the stimulus does not contribute to depolarization. As described herein, a waveform indicative of fusion may be referred to as a "fusion beat" and a waveform indicative of pseudofusion may be referred to as a "pseudofusion beat".

Figure 4:
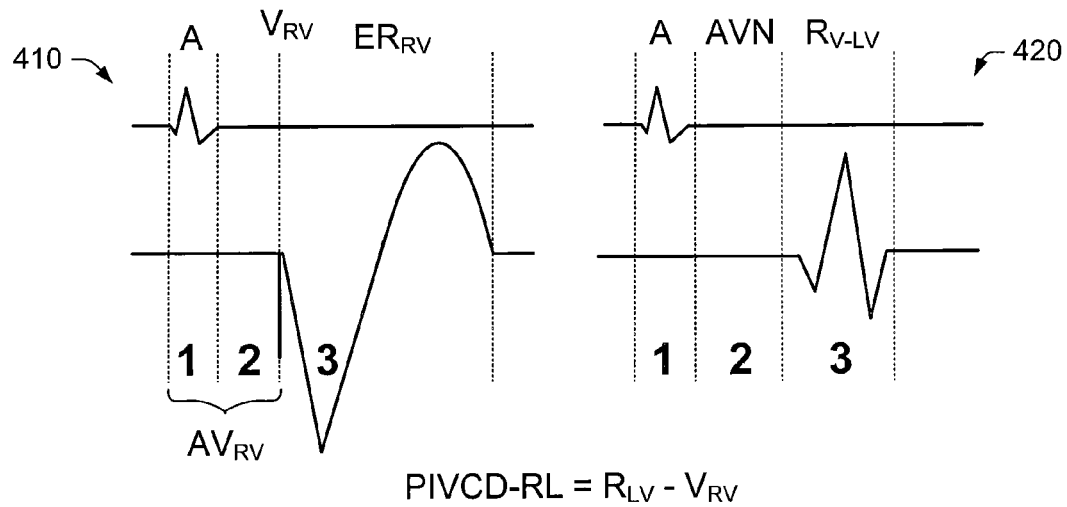
FIG. 4 is an approximate anatomical diagram of a heart and two waveforms that exhibit a paced interventricular conduction delay (PIVCD).
Figure 4:
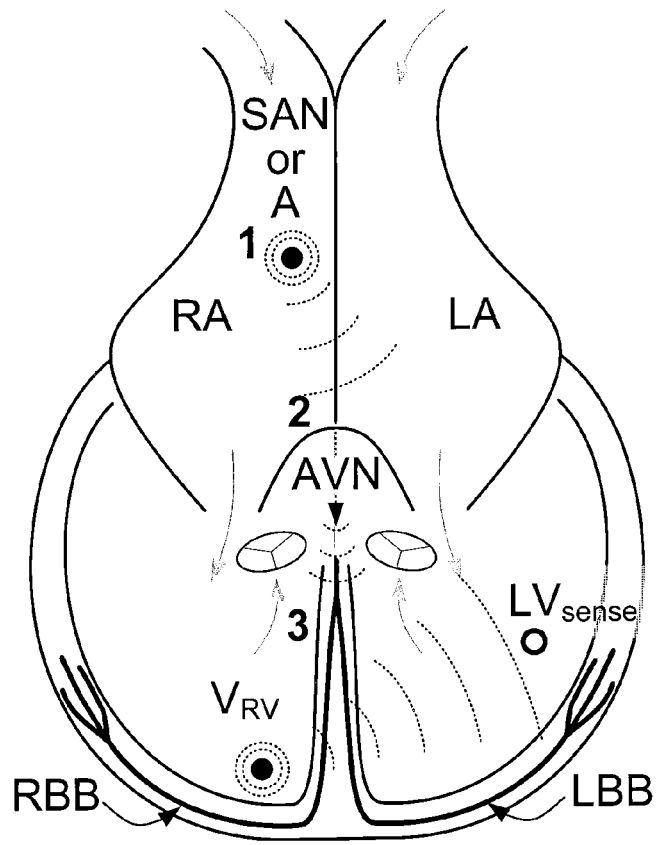

An example of the aforementioned $R_V$ wave or conducted evoked response ($ER_c$) is presented in FIG. 4 (Interventricular Conduction 400), which shows waveform sets (410 and 420), an approximate anatomical diagram and equations associated with a delay time referred to as an interventricular conduction delay (IVCD) and, in this example, a paced interventricular conduction delay (PIVCD). The approximate anatomical diagram includes a right bundle branch (RBB) and a left bundle branch (LBB), as discussed herein, one of the branches may have conduction problems such as a conduction block (e.g., RBBB or LBBB). Such problems can cause contraction of the ventricles to become asynchronous.

An interventricular conduction delay (IVCD) may be a sensed interventricular conduction delay (SIVCD) where an intrinsic event in one ventricle conducts to the other ventricle. For example, where atrial activity occurs in the presence of a bundle branch block, the ventricle without block may be expected to depolarize (2° event) followed by the ventricle with block (3° event). Thus, a sensed interventricular conduction delay may be the interval R to $R_c$ (e.g., SIVCD=$R_c$-R).

Referring to the delay time PIVCD-RL of FIG. 4, this parameter is the difference between the delivery time (e.g., $V_{RV}$) of a ventricular stimulus in one ventricle and contraction of the other ventricle due to interventricular conduction of the delivered ventricular stimulus (e.g., $R_V$). This delay may also be measured from the detection of an evoked response (e.g., $ER_{RV}$) in the ventricle where the stimulus is delivered to the detection of an $R_V$ wave (or $ER_c$) in the other ventricle. Appropriate adjustments may be made depending on the specific technique used.

The scenario of FIG. 4 pertains to pacing in a right ventricle (e.g., $V_{RV}$) and sensing in a left ventricle (e.g., $LV_{Sense}$ location to sense $R_{V-LV}$) where the time between pacing and sensing is referred to as a right to left PIVCD or PIVCD-RL, which equals $R_{V-LV}-V_{RV}$, wherein $V_{RV}$ is a pace time of a pacing stimulus in the right ventricle and $R_{V-LV}$ is a sense time of a "right ventricle, evoked response wavefront" in the left ventricle due to the paced stimulus in the right ventricle. In general, this wavefront is co-extensive with depolarization of the left ventricle and hence referred to as an $R_V$ wave or $ER_c$, as already discussed.

The parameter PIVCD-RL is normally greater than zero. To ensure that the pacing stimulus in the right ventricle results in an evoked response, a capture routine or algorithm may be implemented. Thus, various exemplary methods, devices and/or systems optionally include a capture algorithm (e.g., consider the AUTOCAPTURE™ algorithm of St. Jude Medical, Sylmar, Calif.).

In FIG. 4, the set of waveforms 410 include an atrial event (while labeled "A", this could be a native event e.g., "P"), an atrial to ventricular paced delay $AV_{RV}$, a ventricular pace time $V_{RV}$ and a sensed evoked response in the right ventricle $ER_{RV}$. The other set of waveforms 420 pertains primarily to the left ventricle and includes an atrial event (e.g., A or P), an AVN delay and a sensed evoked response in the left ventricle $R_{V-LV}$ which is a result of the stimulus $V_{RV}$ in the right ventricle. To ensure that the sensed evoked response in the left ventricle $R_{V-LV}$ is not due to conducted electrical activity from the atria, a sufficiently short ventricular paced delay $AV_{RV}$ may be used. For example, a paced delay $AV_{RV}$ of approximately 30 ms to approximately 70 ms may suffice. In one example, $AV_{RV}$ is set to approximately 50 ms to approximately 80 ms. $AV_{RV}$ may also be set sufficiently short to avoid fusion, if conduction exists from the atria to the right ventricle. While AV is referred to, PV may also apply where appropriate.

In general, bipolar sensing (or other multipolar/combipolar sensing) may increase signal to noise of the sensed activation in the left ventricle when compared to unipolar sensing that includes use of an in vivo, yet non-local electrode such as a pulse generator can. The latter technique is more often used in detection of evoked response or applications utilizing far-field signals. Further, bipolar sensing that includes two electrodes positioned in proximity to each other (e.g., less than approximately 4 cm), may increase signal to noise and sensitivity and better sense timing of an activation wave front proximate to the electrodes.

Various delays and other parameters are discussed herein such as the following delays that are related to pacing in the right ventricle and/or the left ventricle:

| | |
|---|---|
| PV | Delay between an atrial event and a paced ventricular event |
| $PV_{optimal}$ | Optimal PV delay |
| $PV_{RV}$ | PV delay for right ventricle |
| $PV_{LV}$ | PV delay for left ventricle |
| AV | Delay for a paced atrial event and a paced ventricular event |
| $AV_{optimal}$ | Optimal AV delay |
| $AV_{RV}$ | AV delay for right ventricle |
| $AV_{LV}$ | AV delay for left ventricle |
| Δ | Estimated interventricular delay, e.g., via IEGM, etc. |
| $\Delta_{programmed}$ | Programmed interventricular delay (e.g., a programmed VV delay) |
| $\Delta_{optimal}$ | Optimal interventricular delay, e.g., via hemodynamic sensing/sensor or other cardiac sensing |
| IVCD-RL | Delay between paced/sensed RV and sensed LV |
| IVCD-LR | Delay between paced/sensed LV and sensed RV |
| $\Delta_{IVCD}$ | Interventricular conduction delay (paced, sensed, hybrid) |

Other parameters include those already mentioned (e.g., $R_V$ or $ER_c$) as well as those conventionally used in conjunction with cardiac activity (e.g., AR, PR, etc.). In addition, parameters such as $AR_V$ or $PR_V$ and yet others, described below, may be used.

Figure 5:
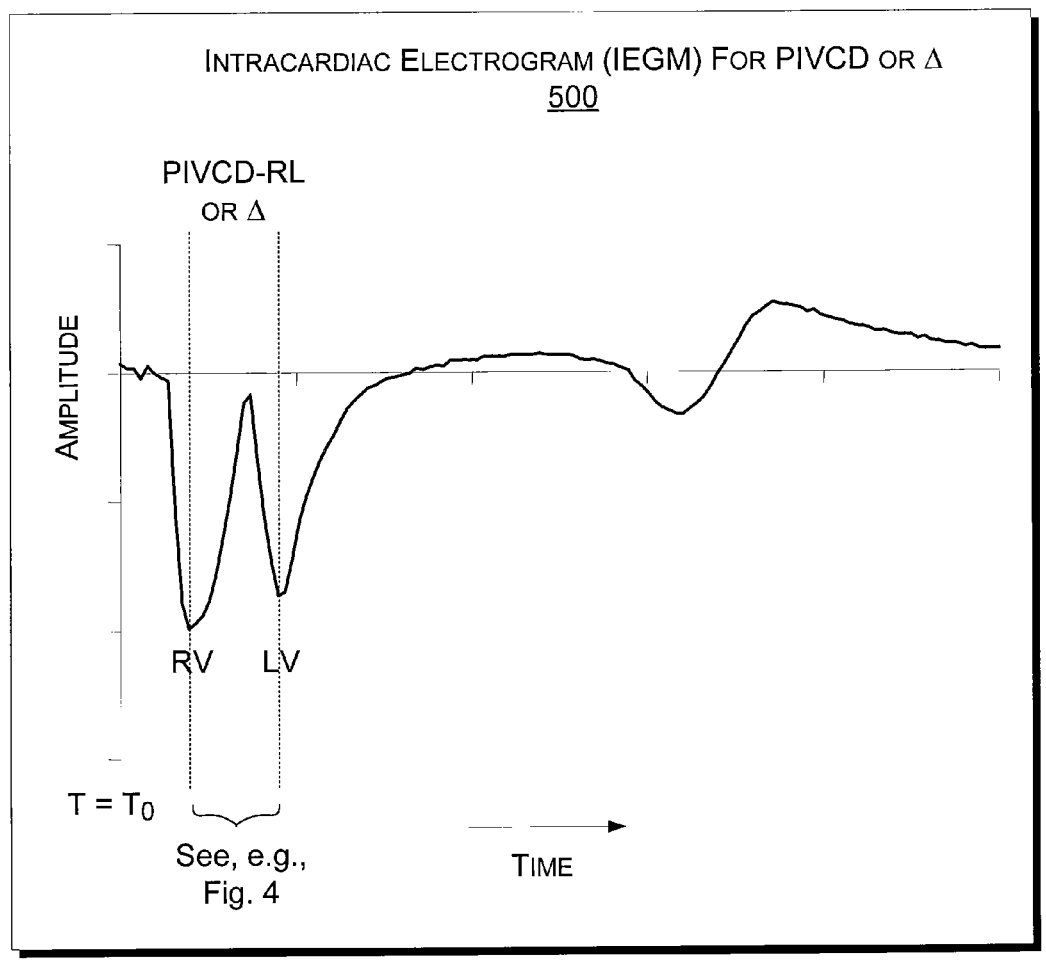
FIG. 5 is an intracardiac electrogram (IEGM) that includes a waveform associated with the right ventricle and a waveform associated with the left ventricle that may be used to determine a paced interventricular conduction delay (PIVCD) or an interventricular delay ($\Delta$). The IEGM was acquired using a unipolar sensing arrangement for a right ventricular tip electrode and a left ventricular tip electrode having a common electrode.

FIG. 5 shows an exemplary IEGM plot 500 acquired in a study using a unipolar sensing arrangement for a right ventricular tip electrode and a left ventricular tip electrode having a common electrode (e.g., can, device sensing circuit, etc.). In this unipolar arrangement, an electrical connection exists between right and left ventricular sensing circuits. In particular, depolarization due to atrio-ventricular intrinsic conduction was sensed at the right ventricle and then sensed at the left ventricle as the activation propagated (i.e., conducted) from the right ventricle to the left ventricle. Even without an electrical connection between RV and LV sensing circuits, an implantable device may provide such IEGM information where depolarization of the RV inscribes a waveform complex and then, upon depolarization of the LV, a second waveform complex is inscribed.

In the example of FIG. 5, a trough-to-trough time delay typically approximates $\Delta$.; noting that peak-to-peak or other feature(s) may be used to approximate $\Delta$. For purposes of discussion, "peak-to-peak" will refer to any of the possibilities for approximating $\Delta$. Referring again to FIG. 5, the delay may approximate PIVCD-RL as in the case of FIG. 4. If RV is paced at a short AV interval, the time delay from pacing RV to the peak of the conduction to the left ventricle approximates PIVCD-RL. In an alternative example, not shown in FIG. 5, a pacing stimulus was delivered to the right ventricle at a time of approximately 0 ms. This pacing stimulus resulted in capture of the right ventricle and the IEGM showed a corresponding right ventricular evoked response. In this example, the left ventricle was not paced or initially captured by the pace to the right ventricle but after a short delay, the left ventricle depolarized spontaneously due to conduction of the paced event from the right ventricle ($R_{V-LV}$). Hence, the delay between the right ventricular peak (RV) and the left ventricular peak (LV) approximates a paced interventricular conduction delay from right ventricle to left ventricle (see, e.g., PIVCD-RL of FIG. 4). Thus, the plot 500 helps to demonstrate a particular exemplary manner in which an implantable device that uses a single sensing amplifier for right and left ventricular sensing channels can determine paced interventricular conduction delay and thus, various parameters. In addition, such a sensing arrangement may be used to determine a VV delay (e.g., $\Delta$, etc.) based on an intrinsic or a paced atrial event that is then conducted to the left ventricle and the right ventricle. This situation is predicated upon the sensing circuit have an extremely short or virtually zero refractory period, particularly an absolute refractory period (i.e., blanking period) such that the circuitry can sense shortly after delivery of a paced stimulus to the RV for sensing of the RV depolarization.

Further, some implantable devices having sensing and pacing capabilities can deliver a stimulus to one ventricle and then switch to sensing of both ventricles. For example, in the plot 500, the RV stimulus may have been delivered in an open configuration (e.g., RV and LV leads/electrodes not "connected") and, thereafter, leads/electrodes "shorted" to allow for sensing from both ventricles. Of course, where appropriate, pacing in one ventricle and sensing in the other ventricle may occur according to various arrangements.

Figure 6:
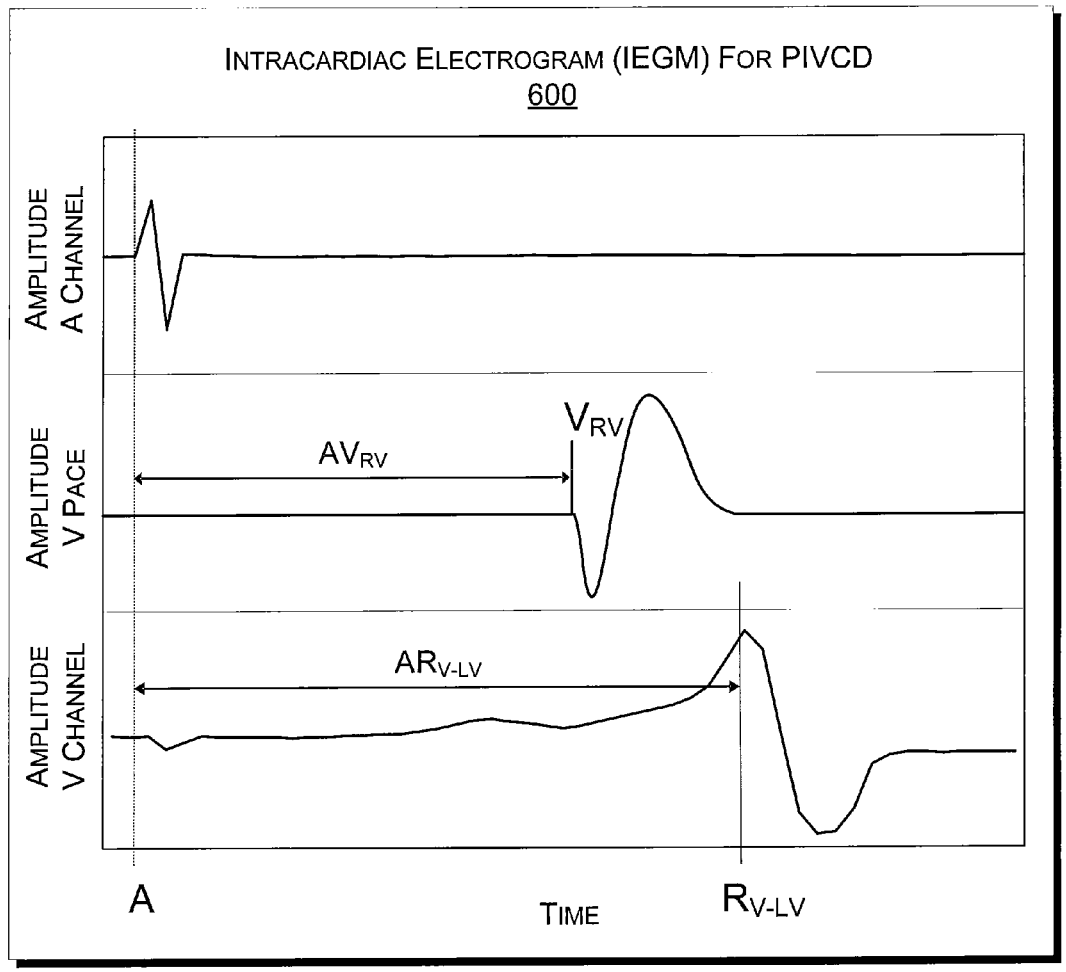
FIG. 6 is an intracardiac electrogram (IEGM) acquired in a study using an implantable device that included a switchable channel for RV and LV sensing and/or pacing. The IEGM shows activation of one ventricle in response to stimulation delivered to the other ventricle; such an IEGM may be used to measure a paced interventricular conduction delay (PIVCD).

FIG. 6 shows an exemplary IEGM plot 600 wherein the ventricular IEGM was acquired in a study using an implantable device including a switchable channel for RV and LV sensing; an equation for PVICD-RL 610 is also shown. Such a device may allow for measurement of $AR_{RV}/PR_{RV}$ and $AR_{LV}/PR_{LV}$ by switching between RV sensing to LV sensing. Accordingly, $\Delta$ may be ascertained. Such a device may also allow for pacing in the right ventricle and/or left ventricle. Further, such a device may ascertain PIVCD-RL and/or PIVCD-LR and optionally $\Delta_{IVCD}$ (the difference between PIVCD-RL and PIVCD-LR). For example, if an $AV_{RV}$ or $PV_{RV}$ interval is set short enough to avoid fusion (i.e., from conduction of an atrial event), then $AR_{V-LV}$ or $PR_{V-LV}$ may be determined on the basis of LV sensing wherein the LV sensing sense electrical activity in the left ventricle (e.g., $R_{V-LV}$) stemming from the right ventricular stimulus (e.g., $V_{RV}$). In this example, PIVCD-RL may equal $AR_{V-LV}-AV_{RV}$ or $PR_{V-LV}-PV_{RV}$. While various examples mention PIVCD, where suitable, SIVCD may be used. Further, in some instances $\Delta_{IVCD}$ may be a hybrid of a PIVCD time and a SIVCD time.

Other implantable devices may include RV and LV sensing channels that can operate at the same time. Such devices may allow for measurement of $AR_{RV}/PR_{RV}$ and $AR_{LV}/PR_{LV}$ on a beat-by-beat basis. For example, for a single beat, an atrial to right ventricular delay and an atrial to left ventricular delay may be ascertained. Such an exemplary method can reduce measurement error by determining such variable for a single beat as compared to determining one variable for one beat and another variable for a different beat. Detection of an event may be based on sensitivity programmed in devices or a criterion such as an amplitude value greater than approximately 40% of an expected QRS amplitude value.

Various exemplary methods, devices and/or systems may help to avoid cross ventricular sensing. For example, if an interventricular delay is less than interventricular conduction (e.g., PIVCD-RL and PIVCD-LR), the incidence of sensing paced ventricular events in an alert interval is reduced. Further, this incidence may be further reduced through use of an automatic capture algorithm.

As already mentioned, fusion is typically characterized by a wave complex formed by depolarization of the myocardium initiated by two different foci, commonly a non-intrinsic stimulus as from a pacemaker or ICD and an intrinsic stimulus. Table 2, below, sets forth various fusion scenarios where stimuli and/or consequences thereof may cause fusion.

TABLE 2

Exemplary Fusion Scenarios

| Scenario | Stimulus | Fusion Chamber | Parameters |
|---|---|---|---|
| 1 | P or A to RV; pace RV | RV | $AVF_{RV}/PVF_{RV}$ |
| 2 | P or A to LV; pace LV | LV | $AVF_{LV}/PVF_{LV}$ |
| 3 | P or A to RV conduct to LV; pace LV | LV | Various |
| 4 | P or A to LV conduct to RV; pace RV | RV | Various |
| 5 | RV pace conduct to LV; pace LV | LV/RV | VVF-RL $AVF_{RV}/PVF_{RV}$ |
| 6 | LV pace conduct to RV; Pace RV | RV/LV | VVF-LR $AVF_{LV}/PVF_{LV}$ |

In Table 2, Scenario 1 is for fusion in the right ventricle where a paced stimulus to the right ventricle ($V_{RV}$) fuses with an intrinsic or non-intrinsic atrial stimulus conducted to the right ventricle ($R_{RV}$); Scenario 2 is for fusion in the left ventricle where a paced stimulus to the left ventricle ($V_{LV}$) fuses with an intrinsic or non-intrinsic atrial stimulus conducted to the left ventricle ($R_{LV}$); Scenario 3 is for fusion in the left ventricle where a paced stimulus to the left ventricle ($V_{LV}$) fuses with an intrinsic or non-intrinsic atrial stimulus conducted to the right ventricle ($R_{RV}$) and is delayed in conduction to the left ventricle ($R_{c-LV}$) (e.g., where left bundle branch block may exist and delay conduction of the atrial stimulus to the left ventricle); Scenario 4 is for fusion in the right ventricle where a paced stimulus to the right ventricle ($V_{RV}$) fuses with an intrinsic or non-intrinsic atrial stimulus conducted to the left ventricle ($R_{LV}$) and is delayed in conduction to the right ventricle ($R_{C-RV}$) (e.g., where right bundle branch block may exist and delay conduction of the atrial stimulus to the right ventricle); Scenario 5 is for fusion in the left ventricle where a paced stimulus to the left ventricle ($V_{LV}$) fuses with a paced stimulus to the right ventricle ($V_{RV}$) that subsequently conducts to the left ventricle ($ER_{C-LV}$) and optionally for fusion in the right ventricle where the paced stimulus to the right ventricle ($V_{RV}$) fuses with an intrinsic or non-intrinsic atrial stimulus; and Scenario 6 is for fusion in the right ventricle where a paced stimulus to the right ventricle ($V_{RV}$) fuses with a paced stimulus to the left ventricle ($V_{LV}$) that subsequently conducts to the right ventricle ($ER_{C-RV}$) and optionally for fusion in the left ventricle where the paced stimulus to the left ventricle ($V_{LV}$) fuses with an intrinsic or non-intrinsic atrial stimulus. Thus, Scenarios 5 and 6 can allow for detection of fusion in both ventricles.

Table 2 also shows various parameters that may be determined for the various scenarios. AVF and PVF refer to surrogates or substitutes for AR and PR and VVF-RL and VVF-LR refer to surrogates or substitutes for IVCD-RL and IVCD-LR, which are discussed above. Where "various" is listed in Table 2, sensing and/or other circumstances may determine which parameters may be determined or estimated. In the scenarios 3 and 4, an AR or PR may be determined for one ventricle and an AVF or PVF for the other ventricle.

Various exemplary methods, devices, systems, etc., optionally rely on occurrence of fusion or other interference to determine one or more pacing parameters. In particular, a variety of techniques may be used to analyze cardiac activity for fusion or other interference. Such techniques include traditional fusion detection techniques that rely on slope, amplitude, morphology, etc. For example, morphology discrimination (see, e.g., block 236 of FIG. 2) may be used to detect fusion. Morphology discrimination typically relies on "dynamic template matching" to discriminate between normal and abnormal events (e.g., fusion, intrinsic depolarization, non-intrinsic depolarization, etc.), which may be present in sensed cardiac activity. Morphology discrimination enables a device to examine multiple characteristics of an electrogram (e.g., sensed cardiac activity), as opposed to techniques which may look only at a complex's width, amplitude and/or slew rate; however, such techniques may be used in conjunction with or as alternatives to one or more morphology discrimination techniques. Morphology discrimination allows for a comparison between a complex, or portion thereof, and a template. For example, morphology discrimination may compare a last acquired complex with a predetermined physician-selected patient-specific template. In commercially available implementations of morphology discrimination (MD), a MD algorithm is normally disabled in the setting of a delivered output pulse. In contrast, various exemplary methods described herein may allow for morphology discrimination or other signal characterization following delivery of an output pulse.

Various exemplary methods, devices, systems, etc., described herein pertain to scenarios 3 and 4. In particular, an exemplary method aims to cause scenario 3 or scenario 4 to be present, thus, fusion may be intentional. While the site of fusion is referred to as "LV" or "RV", the site of fusion may be located and optionally controlled. Fusion may optionally occur at the intraventricular septum (IVS). Intentional or controlled fusion may provide benefits, especially for patients subject to cardiac resynchronization therapy (CRT).

Figure 7:
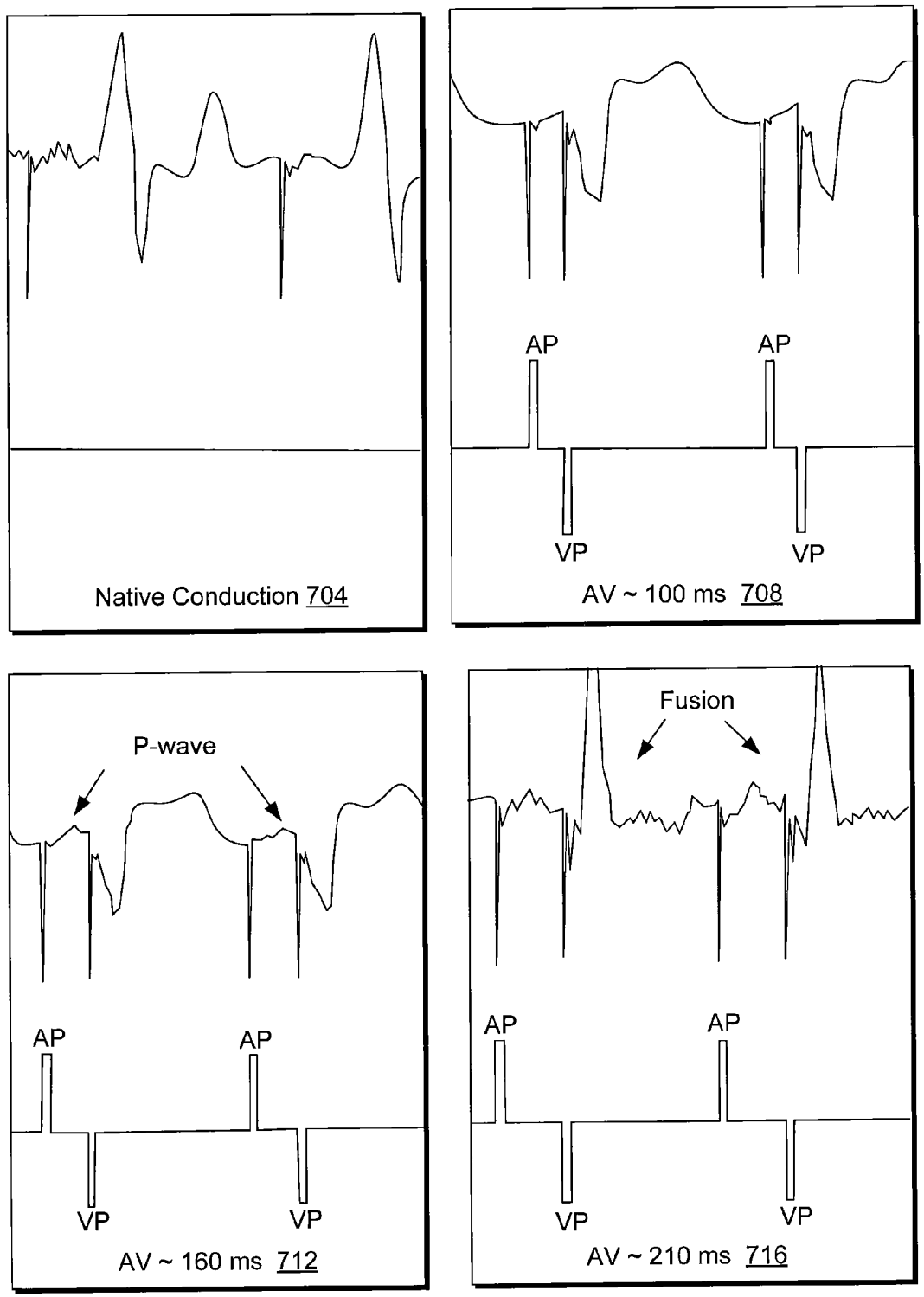
FIG. 7 is a series of electrograms for native conduction and for various atrio-ventricular delays (AV delay) where fusion occurs at one of the AV delays.

FIG. 7 shows four ECGs 704, 708, 712, 716, which correspond to different scenarios. The ECG 704 corresponds to no pacing where native conduction controls, directly or indirectly, contraction of the right ventricle and the left ventricle. The ECG 708 corresponds to pacing with an AV interval of 100 ms, which is a nominal shipped value for a commercially available biventricular pacemaker. The ECG 708 shows that, for an AV interval of 100 ms, there was total loss of AV synchrony. The ECG 712 corresponds to pacing with an AV interval of 160 ms. The ECG 712 shows that the P wave becomes visible in front of the paced QRS and that the paced QRS narrows. The narrowest paced QRS appears in the ECG 716, where an AV interval of 210 ms provided the best velocity time integral (echo measure of stroke volume), which also resulted in fusion with native conduction down the right bundle.

A good percentage of heart patients can have a one sided bundle branch block, i.e., right bundle branch block (RBBB) or left bundle branch block (LBBB), or one sided conduction that is slow whereby such conduction does not provide for adequate cardiac performance. These conditions result in a large inter-ventricular depolarization activation timing difference. For example, a LBBB patient can still have a good conduction from atrium to right ventricular through the AV node to the RBB to the Purkinje RBB. However, starting from somewhere on the path of the Purkinje LBB due to the blockage, the conduction has a larger delay. Thus, the activation of the left ventricle will take an extra time for natural conduction to fully depolarize chamber. In the setting of complete block of the LBB, activation of the left ventricle comes from the depolarization of the right ventricle and then crossing over to the left ventricle by way of the interventricular septum. Consequently, with LBBB, a patient's heart experiences uncoordinated dyssynchronous contraction of the LV. As mentioned in the Background section, CRT aims to address such issues. For example, given an electrode arrangement that allows for pacing at a RV site(s) (e.g., that causes depolarization of the interventricular septum) and at a LV site(s) (e.g., lateral or posterior wall), CRT can synchronize contraction of the LV.

Where pacing occurs, a paced beat takes an extra-time to travel from the pacing site to the rest of heart. For a patient with compromised LBB conduction, pacing at a left ventricular site at correct timing will help synchronize depolarization of the postero-lateral wall of the left ventricle with the interventricular septum, which is depolarized by the naturally conducted impulse. Correct timing may be set according to the time difference of the conduction of RBB and LBB of the intrinsic impulse since this is the time required for the paced depolarization to travel back to the point to meet the depolarization of the other chamber. The equivalent effect is the true cross chamber triggered pacing. However, regular cross chamber triggered pacing can not achieve desired VV synchrony because it can not pre-pace in the chamber with slow conduction. In contrast, "true" cross chamber triggered pacing with advanced pacing can result in the VV synchrony. This phenomenon is demonstrated in the FIG. 8 from data obtained from a patient who has intrinsic RBBB.

Figure 8:
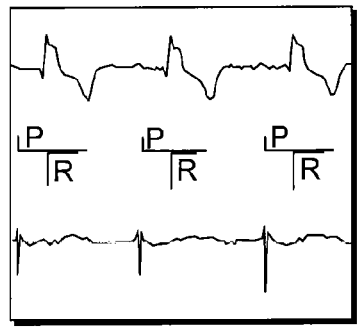
FIG. 8 is a series of electrograms for intrinsic activity, for right ventricular pacing and for intentional fusion.
Figure 8:
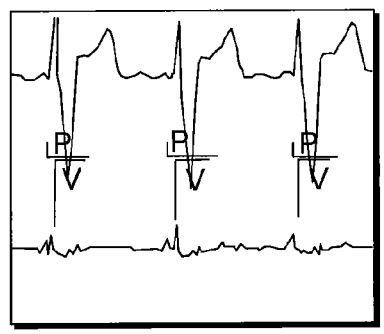
Figure 8:
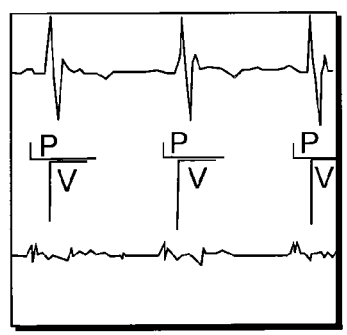

FIG. 8 shows three ECGs 804, 808, 812, which correspond to different scenarios. The ECG 804 shows electrical activity of the heart where the LBB provides an intrinsic conduction pathway, as the patient has RBBB. The ECG 808 shows electrical activity where the right ventricle is paced and where intrinsic conduction causes depolarization of the left ventricle. The ECG 812 shows electrical activity where the timing of the pacing stimulus to the right ventricle is timed such that fusion occurs between the evoked response of the right ventricle and the depolarization of the left ventricle.

Various exemplary methods determine upper and lower limits or boundaries for VV interval or AV/PV interval. For example, an optimal VV interval may be obtained via clinical testing where one ventricle is paced and the other ventricle depolarizes due to intrinsic bundle branch (BB) conduction. Accordingly, the VV interval equals the time difference AR/PR−AV/PV, where AV/PV<AR/PR due to advanced pacing. For a given set of conditions, AR/PR may remain relatively constant and hence the AV/PV time determined via clinical testing may be set as an upper limit. Of course, some margin may be used such as X ms (e.g., a few ms) or a percentage (e.g., 105%) to provide a more flexible boundary; noting, however, that the condition that AV/PV<AR/PR remains. With respect to a lower limit, the minimum AV/PV allowed by an implantable device may be used.

An exemplary method may periodically (or upon occurrence of an event) search for a rate adaptive, dynamic AV/PV where the search extends and/or shortens the paced AV/PV interval so that the paced depolarization will fuse with the sensed AR/PR in the opposite chamber.

An exemplary method for determining an AV/PV interval uses the following equation (Eqn. 1):

$$AV/PV_{programmed} = AR/PR_{measured} - VV_{optimal} + C_{VV} \quad (1)$$

where $C_{VV}$ is a correction factor (positive, negative or zero).

According to this method, the dynamic AV/PV time interval can be further modulated by the instant heart rate, the immediate atrioventricular conduction history, or other information. A particular example uses instant heart rate and the immediate atrioventricular conduction history to modulate a dynamic AV/PV time. With respect to the conduction history, in general, information acquired during the past 24 hours is used; however, depending on patient specifics, this time may consider information acquired past 24 hours.

With respect to detection of fusion or, in general, analysis of electrical activity, techniques disclosed in U.S. Pat. No. 6,928,326 entitled "Diagnosis of Fusion or Pseudofusion", to Levine, issued Aug. 9, 2005, which is incorporated by reference herein ("the '326 patent"), may be used.

As stated in the '326 patent, while fusion and pseudofusion avoidance can improve some pacing therapies, other pacing therapies can benefit from algorithms that help promote fusion. For example, some multisite pacing therapies for dilated cardiomyopathy and congestive heart failure actually rely on fusion because the resulting ventricular activation sequence provides the best hemodynamic results. Therefore, various exemplary fusion and/or pseudofusion recognition algorithms can enhance performance of particular pacing therapies. Pacing therapies discussed herein can benefit from the techniques presented in the '326 patent. In particular, the techniques can help to detect fusion where fusion is a goal.

An exemplary method may store AV/PV interval values or other dynamic information related to synchrony verses parameters such as heart rate and natural intrinsic conduction. Analysis of such stored information can help track progression of conduction problems (e.g., bundle branch block) and heart failure disease.

Various exemplary methods aim to promote the heart's natural AV synchrony and reduce unnecessary ventricular pacing that may exacerbate heart failure; promote VV synchrony with the heart's natural activation in the intact chamber to achieve optimal VV function; dynamically adjust VV timing delay to accommodate the change of patient condition; provide information for disease prognosis; and/or reducing energy consumption by reducing pacing requirements (e.g., less pacing required to maintain VV synchrony) and thus prolong battery life.

With respect to clinical testing, standard tissue Doppler (TD) echocardiographic analysis can provide a wealth of information such as septal wall thickness, posterior wall thickness, LV internal diastolic diameter and systolic diameter, ejection fraction, LV mass index, E peak velocity, A peak velocity, E/A peak velocity, E deceleration time, isovolumic relaxation time, etc. A study by Citro et al., ("Left bundle branch block with and without coronary artery disease: which value for a tissue Doppler-derived post-systolic motion?", *Ital Heart J* 2003; 4 (10): 706-712), reported use of the following TD measurements as indexes of regional myocardial function: myocardial systolic peak velocity ($S_m$, m/s), myocardial pre-contraction time (from the onset of the ECG QRS to the beginning of $S_m$) and contraction time (from the beginning to the end of $S_m$) as systolic indexes and myocardial early ($E_m$) and atrial ($A_m$) peak velocities and their ratios, and relaxation time ($RT_m$)—corresponding to the time interval elapsing between the end of $S_m$ and the onset of $E_m$—as diastolic measurements. The study of Citro et al., used TD for analysis of the middle interventricular septum (or "intraventricular" septum or "IVS") and left ventricular (LV) mitral annulus. Various studies show that the earliest site of activation of the normal ventricular wall occurs at the mid-IVS.

As described herein, an exemplary method optionally aims to locate fusion. In particular, data indicate that, for various patients, optimal VV synchrony corresponds to fusion at a location near the intra-ventricular septum. For example, such a method may determine advanced pacing timing (e.g., an advance pacing interval) such that the paced beat induced ventricular depolarization will fuse with the natural conducted beat introduced ventricular depolarization somewhere near the middle of the heart (e.g., at the IVS). In this example, the two depolarization fronts meet together to achieve the VV synchrony while AV synchrony may be optimized by natural conduction. Thus, clinical testing may aim to uncover mechanics of the IVS to determine optimal VV interval. Of course, other regions of the heart may be examined (e.g., LV mitral annulus, etc.) for purposes of optimizing synchrony.

Figure 9:
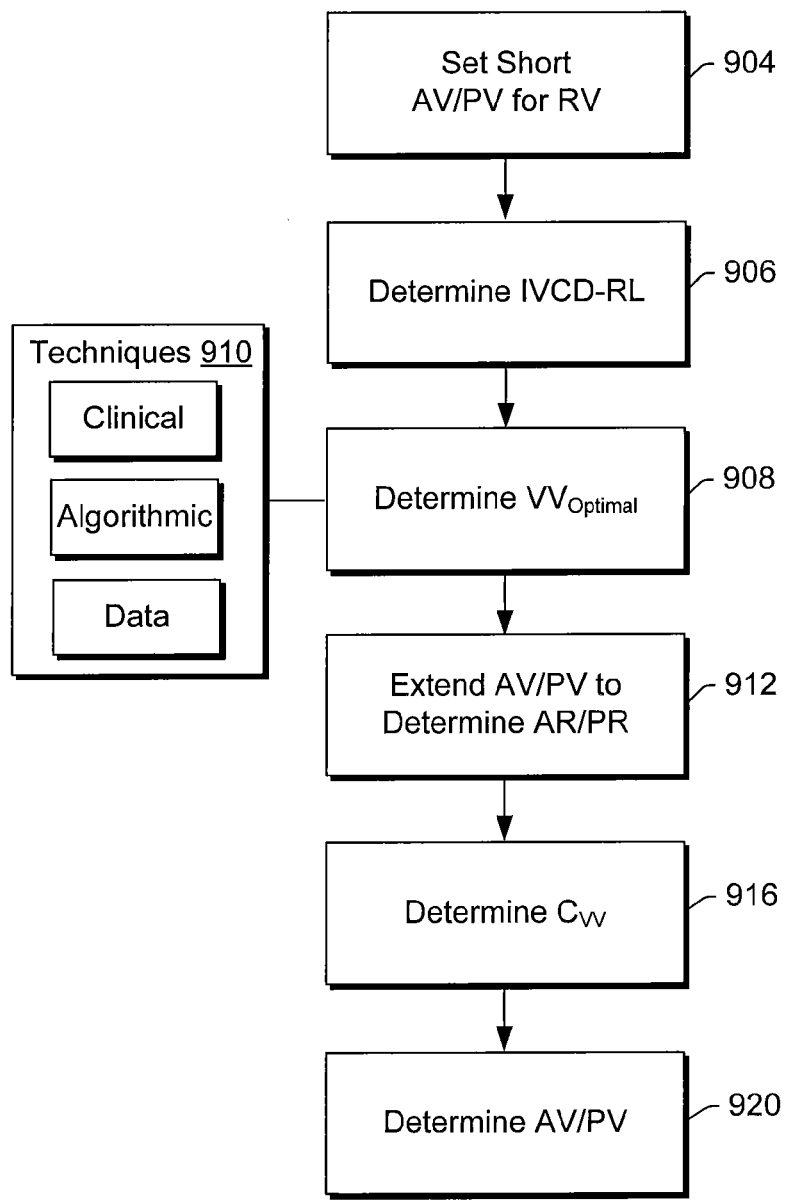
FIG. 9 is a block diagram of an exemplary method for determining an AV or PV delay.

FIG. 9 shows an exemplary method 900 for determining an AV or PV interval. This particular example refers to delivering a stimulus to the right ventricle as conduction to the right ventricle is either faulty (e.g., RBBB) or otherwise too slow. In a set block 904, the AV/PV interval for the right ventricle is set to a value or gradually decreased to a value that allows for conduction of a stimulus to the right ventricle to cause depolarization of the left ventricle. In this example, conduction from atria (or atrium) to the left ventricle is sufficient to cause contraction of the left ventricle. Using the sufficiently short AV/PV interval for the right ventricle, a determination block 906 determines a value for the parameter IVCD-RL (see, e.g., PIVCD-RL of FIG. 4).

The method 900 includes a determination block 908 for determining an optimal VV interval (e.g., $VV_{optimal}$), which may be determined using one or more techniques. A techniques block 910 refers to various techniques, which include clinical techniques, algorithmic techniques, and data-based techniques. For example, a clinical technique may rely wholly or primarily on echocardiograms, an algorithmic technique may rely wholly or primarily on a model that receives values for one or more parameters, a data-based technique may rely wholly or primarily on a database with patient or other data. The determination block 908 may rely on one or more of such techniques or other techniques.

Another determination block 912 extends the AV/PV interval to determine AR/PR interval for the ventricle having sufficient conduction (e.g., the left ventricle). Yet another determination block 916 determines a correction factor (see, e.g., $C_{VV}$ of Eqn. 1) for use in determining an advance AV/PV pacing interval for the right ventricle. For example, the correction factor may be determined using the following equation (Eqn. 2):

$$C_{VV} = (IVCD-RL - VV_{optimal})/IVCD-RL \quad (2)$$

Given the correction factor, the method 900 then enters a determination block 920 to determine the AV/PV interval for advance ventricular pacing of the right ventricle. This block may determine the interval using, for example, the following equation (Eqns. 3A and 3B):

$$AV\ advance = (AV\ interval) - (IVCD-RL) * (1 - C_{VV}) \quad (3A)$$

$$PV\ advance = (PV\ interval) - (IVCD-RL) \times (1 - C_{VV}) \quad (3B)$$

An exemplary method includes providing an optimal interventricular interval, setting an atrio-ventricular interval for the left ventricle or the right ventricle, delivering stimulation to the left ventricle or the right ventricle and sensing cardiac activity of the right ventricle or the left ventricle, respectively, extending an atrio-ventricular interval for the right ventricle or the left ventricle and, if the extending results in atrio-ventricular conduction of an atrial event that causes depolarization of the right ventricle or the left ventricle, respectively, then determining an advance atrio-ventricular pacing interval for the left ventricle or the right ventricle based on the optimal interventricular interval, the delivering and the sensing, and the extending. Such an exemplary method may optionally diagnose right or left bundle branch block if the extending does not result in atrio-ventricular conduction of an atrial event that causes depolarization of the right ventricle or the left ventricle, respectively.

Figure 10:
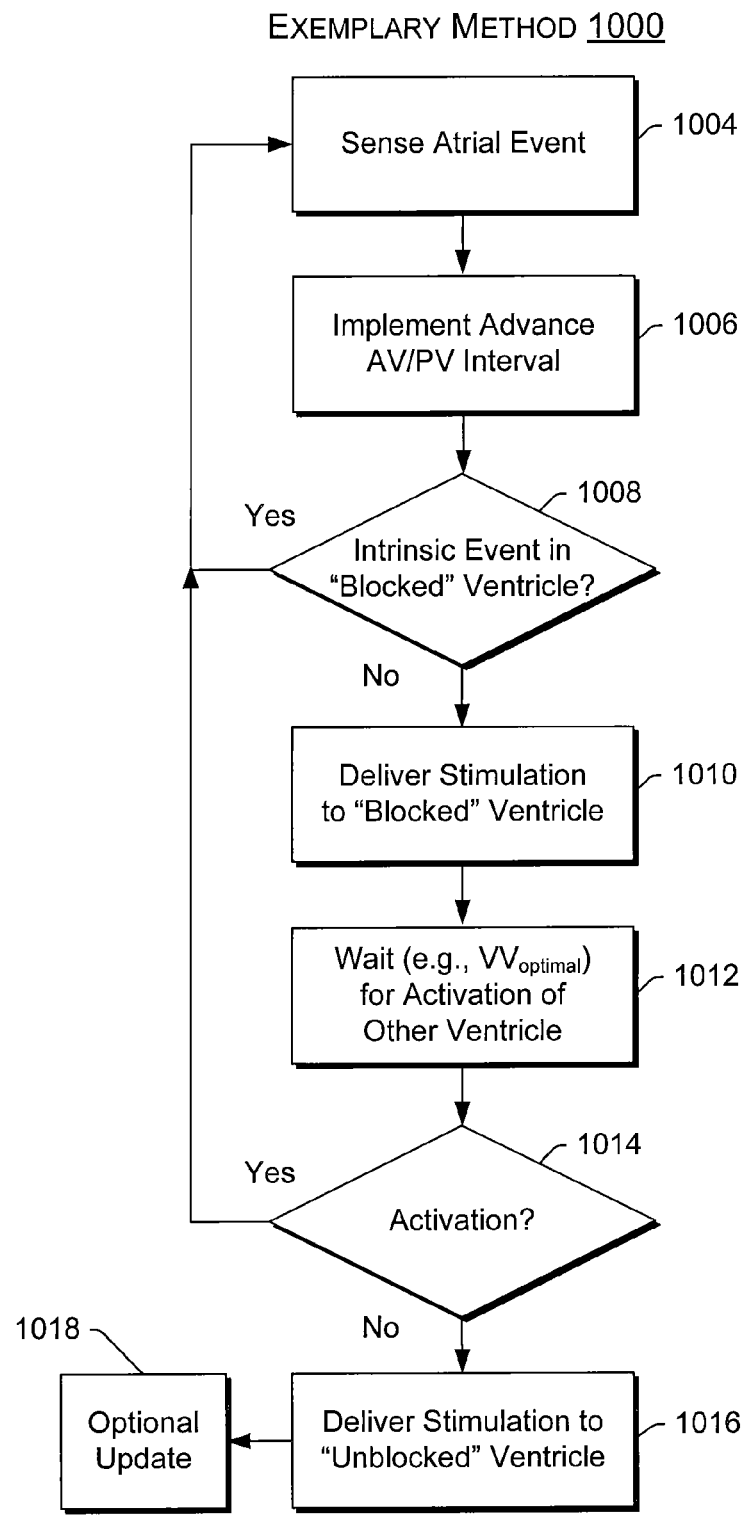
FIG. 10 is a block diagram of an exemplary method for delivering a stimulation therapy that aims to promote bi-ventricular synchrony.

FIG. 10 shows an exemplary method 1000 for optimizing ventricular synchrony. The method 1000 commences in a detection block 1004, upon detection of an atrial event. In response to detection of the atrial event, an implementation block 1006 implements an advance AV/PV interval. As described above, the advance AV/PV interval aims to deliver stimulation to a ventricle with faulty conduction (e.g., bundle branch block or otherwise slow conduction). A decision block 1008 follows implementation of the advance AV/PV interval that relies on sensing to decide if an intrinsic event occurred in the "blocked" ventricle during the advance AV/PV interval. If the decision block 1008 decides that an intrinsic event occurred, then the method 1000 continues in the detection block 1004, where sensing is used to help detect a subsequent atrial event. However, if the decision block 1008 decides that no intrinsic event occurred during the advance interval, then the method 1000 continues in a delivery block 1010 that calls for delivery of stimulation to the "blocked" ventricle.

To proceed, the method 1000 relies on a VV interval, such as the aforementioned $VV_{optimal}$ interval. In particular, a wait block 1012 implements a wait period that waits for activation of the other ventricle, i.e., the "unblocked" ventricle. During this wait period, a detection algorithm relies on sensed information for detection of activation of the other ventricle. The activation may be intrinsic (e.g., of atrial origin) or it may be due to conduction from the "blocked" ventricle. Again, the type of fusion expected by the method 1000 for optimizing ventricular synchrony, is between an artificial activation wavefront of one ventricle and an atrial-to-ventricular activation wavefront of the other ventricle.

A decision block 1014 relies on the detection algorithm to decide if activation occurred during the wait period (e.g., $VV_{optimal}$). If the decision block 1014 decides that activation occurred, then the method 1000 continues at the detection block 1004. However, if it decides that activation did not occur, then the method 1000 enters a deliver block 1016 that calls for delivery of stimulation to the "unblocked" ventricle. Execution of the delivery block 1016 may indicate that some aspect of cardiac condition has changed. Hence, the method 1000 may enter an update block 1018 that aims to update or re-optimize therapy. In instances where the conduction to the "unblocked" ventricle becomes too slow or blocked, then the update block 1018 may simply disable one or more of the fusion-based techniques and revert to delivering stimulation to both ventricles, according to some optimal set of parameters (e.g., AV/PV, VV, etc.).

Referring again to the wait block 1012, the wait period may be set to a value other than $VV_{optimal}$. For example, the following equation (Eqn. 4) may be used to determine the wait period:

$$\text{Wait} = VV_{optimal} + \Omega^*(\text{IVCD-XX} - VV_{optimal}) \qquad (4)$$

where IVCD-XX is the IVCD from the "blocked" ventricle to the "unblocked" ventricle (e.g., PIVCD-RL, PIVCD-LR, SIVCD-RL, SIVCD-LR) and where β is a coefficient, for example between 0 and 1. Equation 4 allows for a wait period that is generally greater than $VV_{optimal}$. The coefficient Ω may be adjusted based, for example, on patient condition, power store, etc. Adjustments of the coefficient can be used to control the frequency or likelihood of bi-ventricular pacing (and single ventricle pacing). In some instances, the coefficient Ω may be assigned a negative value.

Figure 11:
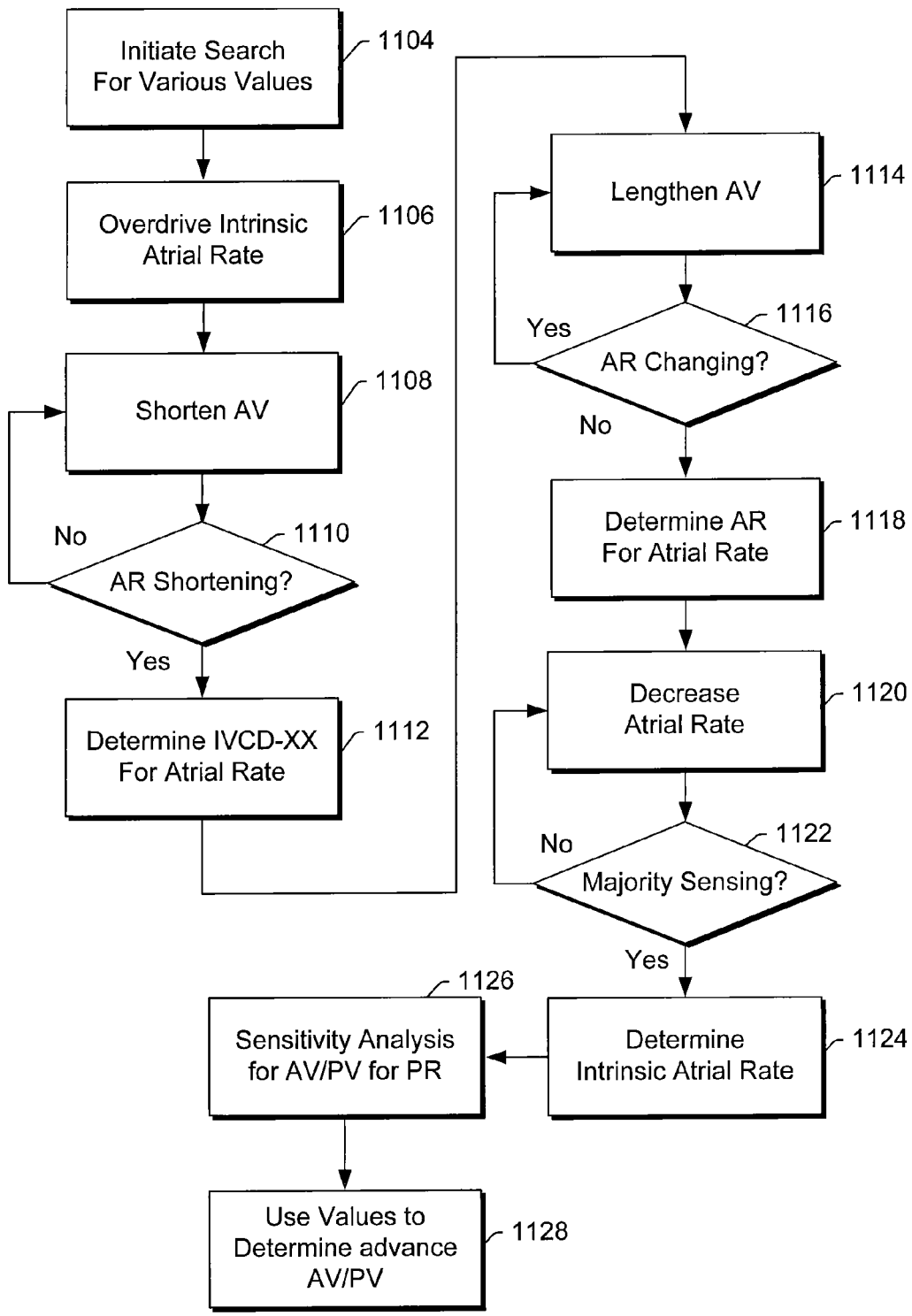
FIG. 11 is a block diagram of an exemplary method for determining various values for use in determining a rate adaptive, advance AV or PV delay.

FIG. 11 shows an exemplary method 1100 that performs various searches for use in determining an advance AV/PV. The method 1100 commences in an initiation block 1104 that initiates a search for various values. These values pertain to the following parameters:

Rate_pacing (atrial rate for majority pacing);

IVCD-XX_delay-rate (where AR interval in "unblocked" ventricle begins to shorten in response to shortening AV/PV of "blocked" ventricle);

AV_delay-rate (where AR in "unblocked" ventricle no longer changes in response to lengthening AV/PV in "blocked" ventricle);

Rate_sensing (atrial rate for majority sensing, i.e., est. intrinsic rate); and

PV delay-rate (rate adaptive intrinsic conduction time based on small changes in AV/PV and not change in AR of "unblocked" ventricle).

The method 1100 continues in an override block 1106 that sets the atrial pacing rate to a value that exceeds and, thus, overdrive, the intrinsic rate. The parameter Rate_pacing is then accorded the override rate. While pacing at the overdrive rate, an action block 1108 acts to shorten the AV for the "blocked" ventricle and, in response, an associated decision block 1110 decides if AR shortening occurs in the "unblocked" ventricle. A loop exists between the decision block 1110 and the action block 1108 that may expire upon a certain amount of AR shortening or upon a certain number of iterations (or other event).

Once AR shortening is noted, a value for the parameter IVCD-XX_delay-rate is determined that corresponds to the interventricular conduction interval from, for example, the paced, "blocked" ventricle to the "unblocked" ventricle. The method 1100 continues in an action block 1114 that acts to lengthen the AV interval for the "blocked" ventricle until a change in AR occurs for the "unblocked" ventricle, as decided by a decision block 1116. Once a change occurs, per the decision block 1116, then a determination block 1118 sets the last unchanged AR, for the given atrial rate, as the rate adaptive intrinsic conduction time AV_delay-rate.

Following the determination block 1118, an action block 1120 acts to decrease the atrial rate until majority sensing occurs (e.g., majority intrinsic atrial control), as decided by a decision block 1122. A determination block 1124 then determines the intrinsic atrial rate (the parameter Rate_sensing) based on the atrial rate where majority sensing occurred. A sensitivity analysis block 1126 follows that shortens and then lengthens the PV (assuming intrinsic control) in small steps and, in response, measures PR intervals in "unblocked" ventricle, until the PR interval no longer changes. The value for the last unchanged PR is then set to be the rate adaptive intrinsic conduction PR time, i.e., the parameter PV delay_rate.

The determination block 1128 then uses the various values to determine the rate adaptive advance AV/PV (ra-advance AV/PV). For example, the following equations (Eqns. 5A and 5B) may be used to determine the advance AV or advance PV:

$$\text{ra-advance AV} = (\text{AV delay\_rate}) - (\text{IVCD-XX\_delay-rate})*(1-C_{VV}) \quad (5A)$$

$$\text{ra-advance PV} = (\text{PV delay\_rate}) - (\text{IVCD-XX\_delay-rate})*(1-C_{VV}) \quad (5B)$$

The exemplary method 1100 or any associated search can be a timer based periodic search, a search that occurs when there is a cardiac rate change (when rate responsive adaptive VV is on) and may be occur when the current rate has not been recorded previously.

Information acquired during execution of the exemplary method 1100 or a part thereof may be used for diagnostics. For example, a method may record the rate adaptive IVCD-XX_delay-rate and AV/PV interval in the form of histogram suitable for trend analysis (e.g., rate, ra-adaptive AV/PV, IVCD-XX_delay-rate and date may be recorded).

Another exemplary method uses sensing in both ventricles. In this example, earliest sensing is expected to occur in chamber which does not have bundle branch conduction delay (i.e., the "unblocked" ventricle). Upon detection of activation in the "unblocked" ventricle, that ventricle is labeled the "first" ventricle or master ventricle. Then, a triggered output is delivered after a programmable delay in the "second" ventricle or slave ventricle. The programmable delay may be 0 ms or some other programmable interval. In this example, synchrony is restored while maintaining the native AV delay and eliminating ventricular pacing to at least one chamber thus effectively reducing battery current drain.

Figure 12:
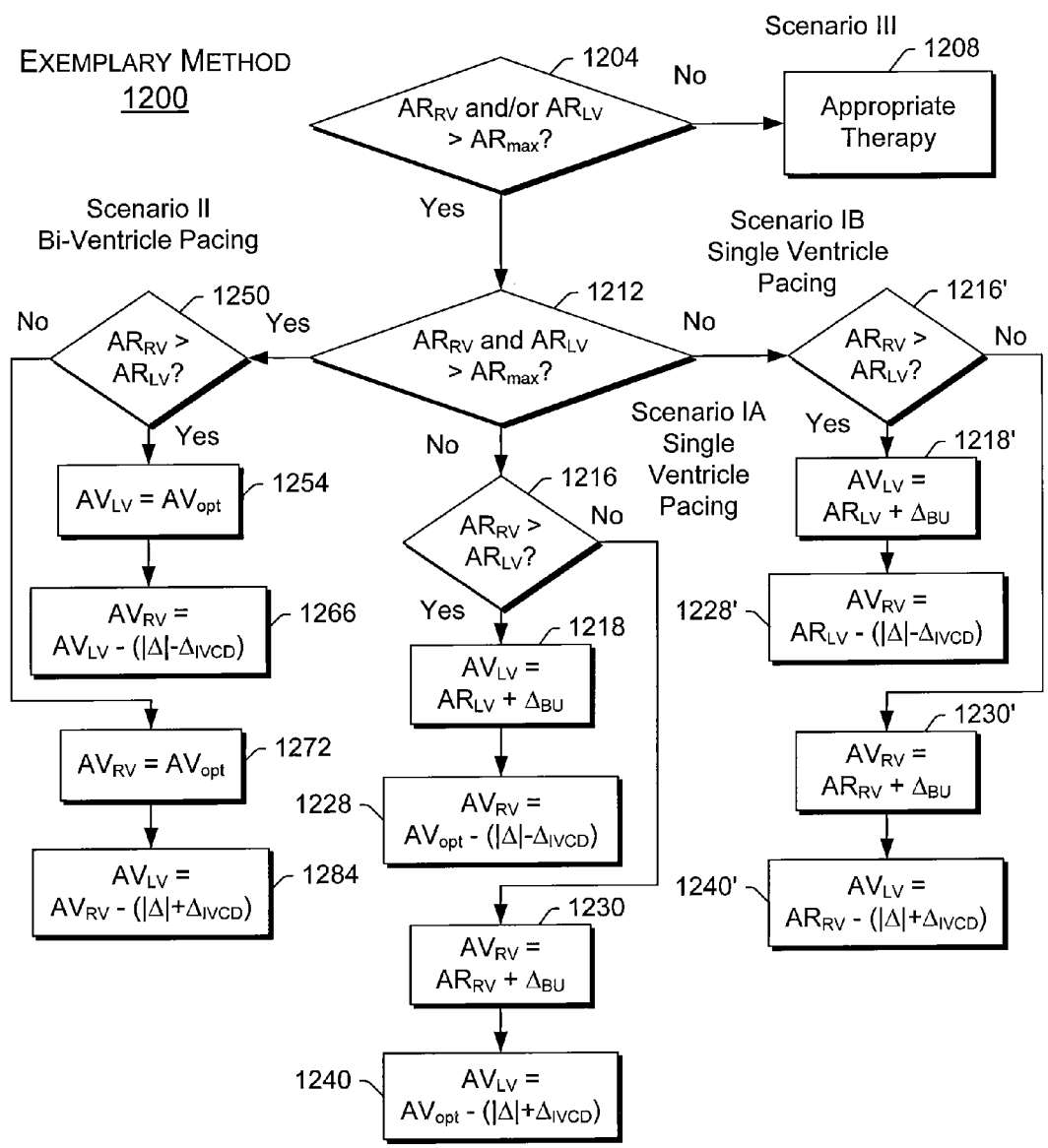
FIG. 12 is a block diagram of an exemplary method that includes various scenarios where therapy may delivery stimulation to both ventricle or to only a single ventricle.

As already mentioned, various techniques may be used to determine the particular pacing method to achieve optimal synchrony. FIG. 12 shows a block diagram of an exemplary method 1200. While the method 1200 pertains to scenarios with atrial pacing, such a method may omit atrial pacing (e.g., rely on an intrinsic atrial activity, etc.) and/or include atrial pacing and intrinsic atrial activity, etc. (e.g., PR, AR, AV, and/or PV). The exemplary method 1200 includes three Scenarios I, II and III.

Figure 13:
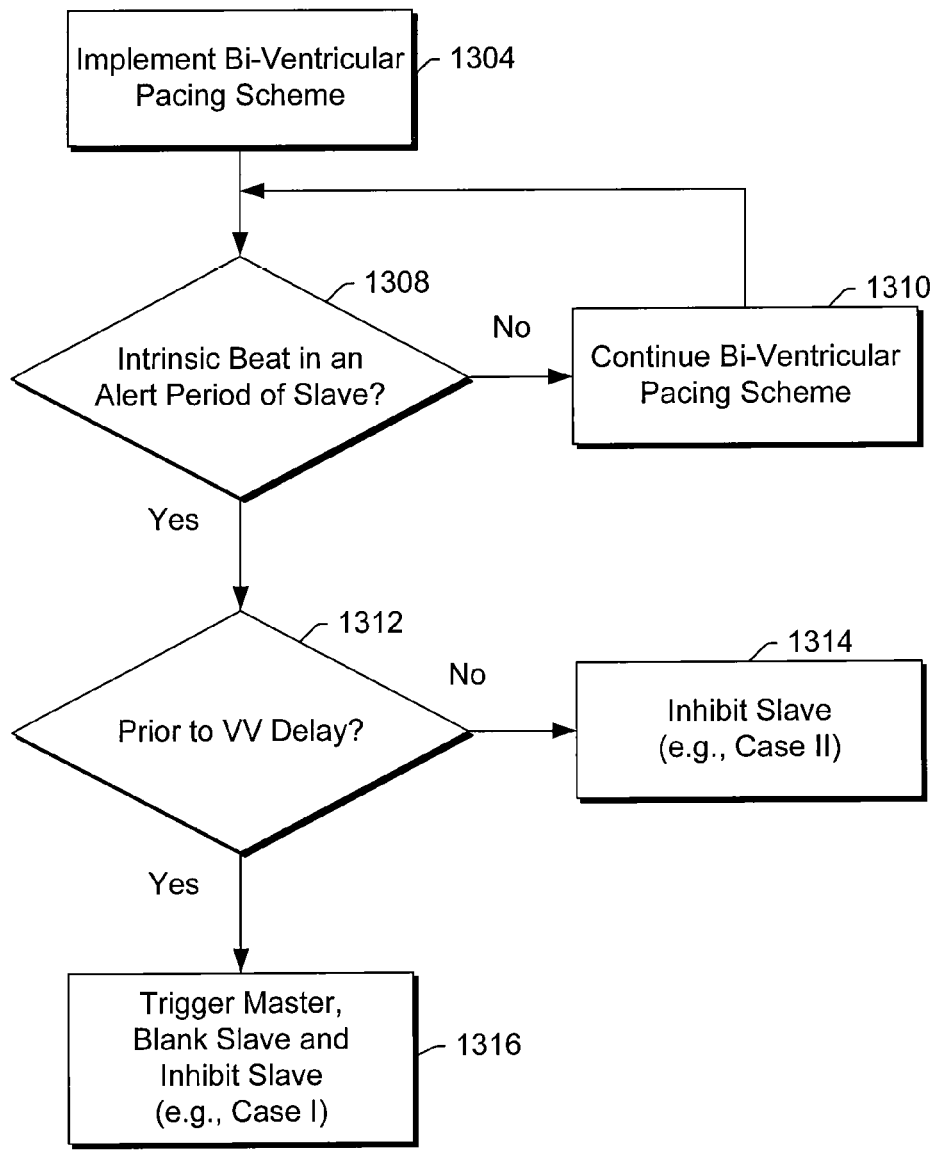
FIG. 13 is a block diagram of an exemplary method that relies on information sensed during an alert period to determine whether bi-ventricular pacing or single ventricle pacing should occur.

With respect to various "fusion" techniques described herein, Scenarios IA and IB: "Single Ventricle Pacing" are of particular interest. For example, the techniques of the methods 900, 1000, 1100 may be applied where single ventricle pacing occurs. FIG. 13, described further below, also includes information germane to single ventricle pacing. An exemplary device optionally includes control logic for performing actions of the method 900, 1000, 1100, 1200 and/or 1300. For example, such a device may be able to perform the actions of the method 1200 and, where single ventricle pacing occurs (Scenarios IA and IB), actions may promote ventricular synchrony via intentional "fusion". Intentional fusion may be suitable for other scenarios as well (e.g., variants of Scenario II, etc.). A discussion of various examples that can include intentional fusion follows a brief description of the method 1200.

According to the method 1200, in a decision block 1204, a decision is made as to whether $AR_{RV}$ and/or $AR_{LV}$ have exceeded a predetermined $AR_{max}$ value. If neither value exceeds $AR_{max}$, then Scenario III follows, which may disable ventricular pacing or take other appropriate therapy per block 1208. Other appropriate therapy optionally includes therapy that achieves a desirable VV delay by any of a variety of techniques. If however one or both values exceed $AR_{max}$, then the method 1200 continues in another decision block 1212. The decision block 1212 decides whether $AR_{RV}$ and $AR_{LV}$ have exceeded $AR_{max}$. If both values do not exceed $AR_{max}$, then single ventricular pacing occurs, for example, per Scenario IA or Scenario IB. If both values exceed $AR_{max}$, then bi-ventricular pacing occurs, for example, Scenario II.

Scenario IA commences with a decision block 1216 that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IA, the method 1200 continues in a back-up pacing block 1218 where $AV_{LV}$ is set to $AR_{LV}$ plus some back-up time (e.g., $\Delta_{BU}$). The block 1218, while optional, acts to ensure that pacing will occur in the left ventricle if no activity occurs within some given interval. The method 1200 then continues in a set block 1228 where the parameter $\Delta_{IVCD}$ is used as a correction factor to set the $AV_{RV}$ delay to $AV_{optimal} - (|\Delta| - \Delta_{IVCD})$.

For left ventricular pacing per the Scenario IA, the method 1200 continues in a back-up pacing block 1230 where $AV_{LV}$ is set to $AR_{LV}$ plus some back-up time (e.g., $\Delta_{BU}$). The block 1230, while optional, acts to ensure that pacing will occur in the left ventricle if no activity occurs within some given interval. The method 1200 then continues in a set block 1240 where the parameter $\Delta_{IVCD}$ is used as a correction factor to set the $AV_{LV}$ delay to $AV_{optimal} - (|\Delta| \Delta_{IVCD})$.

Scenario IB commences with a decision block 1216' that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IB, the method 1200 continues in a back-up pacing block 1218' where $AV_{LV}$ is set to $AR_{LV}$ plus some back-up time (e.g., $\Delta_{BU}$). The block 1218', while optional, acts to ensure that pacing will occur in the left ventricle if no activity occurs within some given interval. The method 1200 then continues in a set block 1228' where the parameter $\Delta_{IVCD}$ is used as a correction factor to set the $AV_{RV}$ delay to $AR_{RV} - (|\Delta| - \Delta_{IVCD})$. Hence, in this example, a pre-determined $AV_{optimal}$ is not necessary.

For left ventricular pacing per the Scenario IB, the method 1200 continues in a back-up pacing block 1230' where $AV_{LV}$ is set to $AR_{LV}$ plus some back-up time (e.g., $\Delta_{BU}$). The block 1230', while optional, acts to ensure that pacing will occur in the left ventricle if no activity occurs within some given interval. The method 1200 then continues in a set block 1240' where the parameter $\Delta_{IVCD}$ is used as a correction factor to set the $AV_{LV}$ delay to $AR_{RV} - (|\Delta| + \Delta_{IVCD})$. Again, in this example, a pre-determined $AV_{optimal}$ is not necessary.

Referring again to the decision block 1212, if this block decides that bi-ventricular pacing is appropriate, for example, Scenario II, then the method 1200 continues in a decision block 1250, which that decides if $AR_{RV}$ is greater than $AR_{LV}$. If $AR_{RV}$ exceeds $AR_{LV}$, then bi-ventricular pacing occurs wherein the right ventricle is the master (e.g., paced prior to the left ventricle or sometimes referred to as left ventricle slave). If $AR_{RV}$ does not exceed $AR_{LV}$, then bi-ventricular pacing occurs wherein the left ventricle is the master (e.g., paced prior to the right ventricle or sometimes referred to as right ventricle slave).

For right ventricular master pacing, the method 1200 continues in a set block 1254 which sets $AV_{RV}$ to $AV_{optimal}$. The method 1200 then uses $\Delta_{IVCD}$ as a correction factor in a set block 1266, which sets $AV_{RV}$ delay to $AV_{LV}-(|\Delta|-\Delta_{IVCD})$.

For left ventricular master pacing, the method 1200 continues in a set block 1272 which sets $AV_{RV}$ to $AV_{optimal}$. The method 1200 then uses $\Delta_{IVCD}$ as a correction factor in a set block 1284, which sets $AV_{LV}$ delay to $AV_{RV}-(|\Delta|+\Delta_{IVCD})$.

As mentioned, conduction issues that affect left ventricle synchrony can have a significant impact on cardiac performance. With respect to the scenarios of FIG. 12, in the decision block 1204, LBBB may cause $AR_{LV}$ to exceed $AR_{max}$. In response, the method 1200 may call for Scenario IA, IB or II. However, an intentional fusion technique may specify a maximum AR or PR for the right and/or left ventricle. Further, such a criterion or criteria for intentional fusion may be chosen in a manner that accounts for the scenarios of FIG. 12. For example, if a cut-off value of 250 ms is chosen for $AR_{max}$ and for intentional fusion, then block 1208 (i.e., Scenario III) may represent an intentional fusion branch of the method 1200. Thus, if a patient (e.g., based on surface ECG), has a PR/AR for the right ventricle and/or the left ventricle less than 250 ms, then the appropriate therapy 1208 could use intentional fusion.

In another example, consider a patient with LBBB, an $AR_{LV}$ greater than the $AR_{max}$ value of the decision block 1204, and an $AR_{RV}$ less than an intentional fusion criterion. In this example, intentional fusion may be used for Scenarios IA, IB or II depending on whether $AR_{RV}$ is greater than $AR_{max}$. Where the cut-off criterion for intentional fusion is the same as $AR_{max}$, then fusion will be used in Scenarios IA or IB as Scenario II would be excluded from intentional fusion. However, if the LBBB conduction issue is intermittent, then an algorithm for Scenario II may allow for intentional fusion where AR is intermittently less than $AR_{max}$ (e.g., intermittent resort to Scenario IA or IB, etc.). For a patient with LBBB, an intentional fusion technique aims to pace the left ventricle in a manner that causes fusion with conducted activity from the RV (or RV pathway).

In yet another example, an AR criterion for intentional fusion is greater than $AR_{max}$ of the decision blocks 1204 and 1212. In such an example, a patient with $AR_{RV}$ and $AR_{LV}$ greater than $AR_{max}$ can use Scenario II with intentional fusion if $AR_{RV}$ and/or $AR_{LV}$ is less than the intentional fusion criterion.

As described herein, a cut-off value for intentional fusion may be based at least in part on an optimal AV delay for a patient. Further, as the optimal AV delay may change over time, a patient may intermittently qualify for CRT that uses one or more intentional fusion techniques. Noting that intentional fusion techniques require AV conduction to at least one ventricle.

In some instances, a patient may have an AR/PR to a ventricle that is quite short and not suitable for purposes of intentional fusion. Accordingly, the method 1200 may include one or more decision blocks for deciding whether AR/PR is too short for implementing an intentional fusion technique. In general, such blocks would normally be associated with Scenarios IA or IB (single ventricle pacing) as decision block 1212 requires $AR_{RV}$ and $AR_{LV}$ greater than $AR_{max}$. However, as mentioned, values can vary with respect to time. Hence, decisions in the method 1200 and other decisions could be repeated over time with different outcomes. Further, a clinician may adjust decision criteria over time.

While various examples pertain to a single RV site or a single LV site for purposes of fusion, an example may include a plurality of RV sites or a plurality of LV sites. For example, if a CRT device includes a lead or leads configured for multiple LV sites, then stimulation energy may be delivered in a coordinated manner to the LV sites to achieve intentional fusion. Alternatively, one site may be selected from the plurality of sites for purposes of achieving intentional fusion. In another example, a CRT may achieve intentional fusion by delivering stimulation energy to one site for some beats and by delivering stimulation energy to a different site for some other beats. In such an example, cardiac performance may be assessed to determine patient condition, effectiveness of CRT, etc.

A comparison between $\Delta$ and $\Delta_{programmed}$ or $\Delta_{optimal}$ can indicate a difference between a current cardiac therapy or state and a potentially better cardiac therapy or state. For example, consider the following equation:

$$\alpha = \Delta_{optimal}/\Delta \qquad (6)$$

where $\alpha$ is an optimization parameter. Various echocardiogram studies indicate that the parameter $\alpha$ is typically about 0.5. The use of such an optimization parameter is optional. The parameter $\alpha$ may be used as follows:

$$AV_{RV} = AV_{optimal} - \alpha|\Delta| \text{ or} \qquad (7A)$$

$$PV_{RV} = PV_{optimal} - \alpha|\Delta| \qquad (7B)$$

$$AV_{LV} = AV_{optimal} - \alpha(|\Delta| + \Delta_{IVCD}) \text{ or} \qquad (8A)$$

$$PV_{LV} = PV_{optimal} - \alpha(|\Delta|\Delta_{IVCD}) \qquad (8B)$$

If a parameter such as the aforementioned $\alpha$ parameter is available, then such a parameter is optionally used to further adjust and/or set one or more delays, as appropriate.

Various exemplary methods, devices, systems, etc., may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equations (Eqn. 9A and 9B) may be used in such a situation:

$$AV_{LV} = AR_{RV} - |\Delta| \text{ or} \qquad (9A)$$

$$PV_{LV} = PR_{RV} - |\Delta| \qquad (9B)$$

Eqn. 9A is similar to the equation used in blocks 1228' and 1240' of Scenario IB of FIG. 12. With respect to backup pulses, a backup pulse (e.g., for purposes of safety, etc.) may be set according to the following equations (Eqn. 10A and 10B):

$$AV_{RV} = AR_{RV} + |\gamma| \text{ or} \qquad (10A)$$

$$PV_{RV} = PR_{RV} + + |\gamma| \qquad (10B)$$

Of course, administration of a backup pulse may occur upon one or more conditions, for example, failure to detect activity in the particular ventricle within a given period of time. In the foregoing equation, the parameter $\gamma$ is a short time delay, for example, of approximately 5 ms to approximately 10 ms. Eqn. 10A is similar to the equation used in blocks 1218' and 1230' of Scenario IB of FIG. 12.

FIG. 13 shows a block diagram of an exemplary method 1300. While the method 1300 pertains generally to bi-ventricular pacing to pace a master ventricle and a slave ventricle, under certain circumstances, pacing is inhibited to the slave ventricle, which results in single ventricle pacing. Specifically, the method 1300 addresses circumstances when an intrinsic beat occurs in an alert period of a slave ventricle. Such an occurrence indicates that intrinsic activity exists and that the timing of the intrinsic activity may suffice for purposes of single ventricle pacing (e.g., including single ventricular pacing with intentional fusion).

According to the method 1300, an implementation block 1304 implements a bi-ventricular pacing scheme. A decision block 1308 follows wherein a decision is made as to whether an intrinsic event has occurred in an alert period of a ventricular channel (e.g., a slave channel). If the decision block 1308 decides that no activity or event has occurred in an alert period, then the method 1300 proceeds to a continuation block 1310 where the bi-ventricular pacing scheme continues where, as appropriate, the method 1300 flows back to the decision block (e.g., after certain programmed events, etc.). However, if the decision block 1308 decides that an intrinsic event occurred in an alert period, then another decision block 1312 follows. The decision block 1312 decides if the activity or event occurred prior to a VV delay period (e.g., a $\Delta_{programmed}$). If the decision block 1312 decides that the occurrence was not prior to a VV delay period then the method 1300 continues in an inhibition block 1314 that inhibits delivery of a pace event to a ventricle. However, if the decision block 1312 decides that the occurrence was prior to a VV delay period then the method 1300 continues in a trigger, blank and inhibition block 1316. The trigger, blank and inhibition block 1316 acts to trigger delivery of a pace to a ventricle (e.g., the master ventricle), to initiate one or more blanking periods (e.g., atrial and/or ventricular), and to inhibit delivery of a pace to the other ventricle (e.g., the slave ventricle).

Of course, an alert period for a master ventricular channel may exist wherein an intrinsic event in the master ventricle causes inhibition of a scheduled pace event in the master ventricle and causes an update in the timing of a scheduled slave pace event. For example, if an intrinsic event is sensed or detected in the master ventricle, then the VV delay may commence in response thereto. Such an exemplary method would act to preserve the VV delay (e.g., $\Delta_{programmed}$) to ensure appropriate timing of contractions in left and right ventricles.

An exemplary method includes setting an interventricular (VV) delay between a master ventricle and a slave ventricle (e.g., setting $\Delta_{programmed}$) and sensing for ventricular activity. If activity is sensed in the slave ventricle prior to the VV delay period and hence prior to delivery of a pace to the master ventricle, then the method may immediately deliver stimulation to the master ventricle and inhibit delivery of stimulation to the slave ventricle. If activity is sensed in the slave ventricle after delivery of stimulation to the master ventricle and prior to expiration of the VV delay, then the exemplary method may inhibit delivery of stimulation to the slave ventricle. Such a method optionally includes adjusting the ventricular refractory period in the slave ventricle channel to be greater than the appropriate IVCD minus VV. IVCD could be either IVCD-LR or IVCD-RL or an average of the two. Such a method optionally switches to single ventricular pacing, where appropriate, and delivers single ventricular pacing to achieve intentional fusion.

An exemplary implantable device includes a power supply, a processor, a lead including one or more electrodes capable of being positioned proximate to a master ventricle, a lead including one or more electrodes capable of being positioned proximate to a slave ventricle, and control logic, executable through use of the processor, to set an interventricular delay between the master ventricle and the slave ventricle and to call for immediate delivery of stimulation to the master ventricle using the lead proximate to the master ventricle upon detection of intrinsic activity in the slave ventricle prior to the interventricular delay (e.g., prior to delivery of stimulation to the master ventricle). Such control logic optionally inhibits delivery of stimulation to the slave ventricle. Such control logic optionally calls single ventricular pacing, where appropriate, and delivers single ventricular pacing to achieve intentional fusion.

An optimal interventricular delay can change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

As described herein, various techniques include adjusting one or more pacing parameters based at least in part on patient activity. Such techniques may use variables such as P wave width ($\Delta P$), A wave width ($\Delta A$), delay from end of a P wave to beginning of a QRS complex (DD or DD interval) and/or delay from end of an A wave to beginning of a QRS complex (AD or AD interval). Two parameters, $\delta$ and $\beta$, are discussed in more detail below. The parameter $\delta$ may depend on $\Delta P$ or $\Delta A$ while the parameter $\beta$ may depend on $\delta$ and DD or AD, as indicated by the following equations:

$$\delta = f(\Delta P) \text{ or } f(\Delta A) \tag{11}$$

$$\beta = \delta/DD \text{ or } \delta/AD \tag{12}$$

These parameters may be used to determine one or more pacing parameters, for example, as indicated by the following equations:

$$PV = \Delta P + \beta * DD \tag{13A}$$

$$AV = \Delta A + \beta * AD \tag{13B}$$

Variations of these four foregoing equations are presented with respect to FIG. 14. The PV or AV forms may be used to determine an optimal PV or AV. For example, $AV_{opt}$ may be determined and then used in any of the various scenarios of FIG. 12. For VV delay, techniques described above may be used. However, as discussed in more detail below, VV may depend on activity and hence may change when activity state changes. Where VV is used for bi-ventricular pacing, the following equations may be used:

$$PV'' = PV' + VV \tag{14A}$$

$$AV'' = AV' + VV \tag{14B}$$

where PV' and AV' are for the master ventricle and where PV" and AV" are for the slave ventricle.

Various exemplary method discussed herein include sensing patient activity, for example, using an activity sensor (e.g., accelerometer, minute ventilation, etc.), and adjusting one or more pacing parameters based at least in part on such sensing. An exemplary method may select a pacing parameter for a pacing therapy based on patient activity state. For example, an implantable device may include a set of parameters for a rest state and a set of parameters for an exercise state.

An exemplary method may include monitoring one or more characteristics of atrial activity and adjusting one or more pacing parameters based at least in part on such monitoring. For example, a method may include monitoring P wave width (e.g., $\Delta P$) and using P wave width to adjust one or more pacing parameters whereas another method may include monitoring A wave width (e.g., $\Delta A$) and using A wave width to adjust one or more pacing parameters. P wave width or A wave width may increase as patient activity increases. Thus, if the P wave width or the A wave width exceed a limit, then an exemplary method may call for a change in one or more pacing parameters.

An exemplary method may include disabling ventricular pacing (for one or both ventricles) and measuring DD interval or AD interval, respectively, and adjusting one or more pacing parameters based at least in part on such measuring. DD interval or AD interval may increase as patient activity increases. Thus, if the DD interval (e.g., $DD_{RV}$ or $DD_{LV}$) or the AD interval (e.g., $AD_{RV}$ or $AD_{LV}$) exceed a limit, then an exemplary method may call for a change in one or more pacing parameters.

An exemplary method may include sensing PP interval as a marker for the atrial rate (from P wave to P wave) which can serve as a surrogate for patient activity and adjusting one or more pacing parameters based at least in part on such sensing. In general, PP interval will decrease as patient activity increases; noting that certain conditions or drugs may make this technique less useful (e.g., beta blockers, high NYHA class, etc.). While PP interval is mentioned, other intervals may be used based on a marker that occurs once per cardiac cycle (e.g., $R_{RV}$, $R_{LV}$, etc.). An exemplary method may select a pacing parameter for a pacing therapy based on an interval. For example, an implantable device may include a set of parameters for a long interval (e.g., a rest state) and a set of parameters for a short interval (e.g., an exercise state).

While the foregoing discussion pertains to schemes individually, an exemplary method may use any of the various schemes, as appropriate. For example, an exemplary method may include monitoring P wave width and disabling ventricular pacing (to one or both ventricles) to measure DD interval based at least in part on P wave width.

FIG. 14 shows various exemplary methods 1400. While equations are presented in FIG. 14, implementation of techniques described herein may be implemented using any of a variety of forms of control logic. For example, look-up tables may be used together with logic that stores and/or pulls data from the look-up table. Control logic to achieve the overall goals achieved by the various equations 1400 may be achieved by control logic that does not explicitly rely on the equations, as presented.

A state block 1410 defines various activity states. The activity states include a base state, for example, a rest state denoted by a subscript "0". In other examples, the subscript "rest" is used. The activity states include at least two states, for example, a base state and another activity state. In FIG. 14, the states range from the base state to activity state "N", which may be an integer without any numeric limitation (e.g., N may equal 5, 10, 100, 1000, etc.). The number of activity states may depend on patient condition and patient activity. For example, a patient that is bedridden may have few activity states when compared to a young patient (e.g., 40 years old) fitted with a pacemaker that leads an active life with a regular exercise regimen.

A PV or AV states block 1420 presents equations for the parameters $\beta$ and $\delta$ as well as for a base state PV and AV and PV and AV for a state other than a base activity state, referred to as $AS_x$, where x=1, 2, ... N. In addition, sets of equations are presented that include a pacing latency term PL. Pacing latency is generally defined as the time between delivery of a cardiac stimulus and the onset of an evoked response caused by the stimulus. More specifically, an implantable device may use the time of delivery of a stimulus and the time at which a sensed, evoked response signal deviates from a baseline, which is referred to herein as $PL_i$ (e.g., to initiation of evoked response). Such a signal is usually sensed using the lead that delivered the stimulus, however, electrode configuration may differ (e.g., unipolar delivery and bipolar sensing, bipolar delivery and unipolar sensing, etc.). In some instances, the pacing latency may exceed 100 ms due to ischemia, scarring, infarct, etc. Thus, PV or AV timing may be adjusted accordingly to call for earlier or later delivery of a stimulus to a ventricle or ventricles.

An exemplary algorithm may determine PL for the right ventricle (for a right ventricular lead) and for the left ventricle (for a left ventricular lead) during measurement of IVCD-LR and IVCD-RL (e.g., parameters that may be used to determine VV). While pacing latency can be measured from the time of delivering a pacing pulse to the time of an evoked response at the pacing lead ($PL_i$), pacing latency may be measured alternatively from the time of the pulse to the peak of an evoked response ($P_{Peak}$). In either instance, such techniques may shorten block and/or discharge periods, optionally to a minimum (e.g., about 3 ms in some commercial ICDs). An algorithm may also provide for detection of capture, for example, using an integral (e.g., PDI) and/or a derivative (e.g., $D_{max}$). In general, pacing latencies for LV and RV leads correspond to situations where capture occurs. In yet another alternative, during P wave and PR measurement, a time delay from a marker of a sensed R event to the peak of a QRS complex may be measured and used as a correction term akin to pacing latency.

A VV states block 1430 presents equations for the parameters a, A and $\Delta_{IVCD}$ and VV for a base activity state ($AS_0$) and another activity state ($AS_x$). As described herein, "VV" represents an interventricular interval that occurs during a single "heartbeat" or cardiac cycle (e.g., from delivery of stimulation energy to the RV to delivery of stimulation energy to the LV for a cardiac cycle); whereas, "PP" represents an interval for atrial activity from one cardiac cycle to a subsequent cardiac cycle. These equations may be used in various scenarios of the method 1200 of FIG. 12 or other methods. Noting that some differences exist between the method 1200 and the equations of FIG. 14, for example, lack of absolute values for the parameter $\Delta$. To account for this variation, the value of $\Delta$ is used to determine whether the right ventricle or left ventricle is paced for single ventricle pacing or is the master for bi-ventricular pacing. If the $\Delta$ is less than 0 ms, then the right ventricle is paced (e.g., RV master) whereas if $\Delta$ is greater than 0 ms, then the left ventricle is paced (e.g., LV master). For bi-ventricular pacing, the PV or AV state equation is used for the master ventricle and then the VV equation is used to determine timing of the slave ventricle. Hence, the control logic uses $\Delta$ to determine whether the PV or AV state equation will correspond to the left ventricle or the right ventricle.

The block 1430 also includes equations for a pacing latency differential, referred to as $\Delta PL$. This term may be calculated, for example, as the difference between $PL_{Peak}$ and a generic or average pacing latency (e.g., $PL_{Ave}$ based on a sampling of "normal" pacing latencies). Hence, $\Delta PL$ may represent a difference from a normal pacing latency. A normal pacing latency may be around 70 ms and hence $\Delta PL$ may equal $PL_{Peak}$ minus 70 ms. The parameter ΔPL may be calculated for both the right ventricle (e.g., ΔPL-RV) and the left ventricle (e.g., ΔPL-LV). Where VV has positive sign that indicates to pace LV first, then the correction term ΔPL-LV may be added while where VV has a negative sign that indicates to pace RV first then the correction term APL-RV may be added. In block 1230, the term APL is shown without indication of LV or RV, noting that use of APL-LV or APL-RV may be determined accordingly. A criterion or criteria may be used to decide if a pacing latency correction term should be used in determining PV, AV or VV. For example, if PL exceeds a certain limit, then a pacing latency correction term or terms may be used. Similarly, if APL exceeds a certain limit, then a pacing latency correction term or terms may be used.

Recent clinical data indicates that during exercise, optimal PV/AV delays are prolonged compared with those at rest in HF patients. Various exemplary techniques described herein can account for changes for HF patients during exercise and at rest through the duration of P wave or A wave and an appropriate atrio-ventricular conduction delay. During exercise some HF patients may have an increase in width of atrial signals or atrio-ventricular conduction delays or both that would lead to prolonged optimal AV and PV delays. In patients with normal rate responses, AV or PV delays may have negative hysteresis or remain the same as at rest.

While various examples mention use of a "rest" state, a rest state may be a base state. Alternatively, a base state may be a state other than a rest state. For example, a base state may correspond to a low activity state where a patient performs certain low energy movements (e.g., slow walking, swaying, etc.) that may be encountered regularly throughout a patient's day. Thus, a base state may be selected as a commonly encountered state in a patient's waking day, which may act to minimize adjustments to PV, AV or VV. Further, upon entering a sleep state, a device may turn off adjustments to PV, AV or W and assume sleep state values for PV, AV or VV. Such decisions may be made according to a timer, a schedule, an activity sensor, etc.

Various exemplary methods, devices, systems, etc., include triggering of an algorithm to update optimal VV delay according to a predetermined time or event period or activity sensors for exercise, resting, etc. An exemplary device may include a learning method that learns based on differences in conduction times (e.g., $AR_{RV}$ and $AR_{LV}$, IVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional. Further, use of internal measurement or sensing equipment for sensing pressure or other indicators of hemodynamic performance is optional. Again, adjustment and learning may rely on IEGM information and/or cardiac other rhythm information.

According to various exemplary methods, devices, systems, etc., information acquired (e.g., sensed, detected and/or determined) may be used to diagnose cardiac condition. For example, an exemplary method may track AV delays and/or VV delays over time. Such information may then be used to determine subsequent therapy.

Various exemplary methods, devices, systems, etc., include determining an optimal interventricular delay (e.g., $Δ_{optimal}$) using a modality such as an echocardiogram. While an internal echocardiogram or implantable hemodynamic sensors may be available or become available and be able to measure such optimal delays for a variety of patient circumstances (e.g., sleep, exercise, etc.), an exemplary method, device, system, etc., includes use of one or more internal sensors to measure and/or update such an optimal delay and/or to determine values for one or more parameters related to an optimal delay. For example, a blood pressure sensor (e.g., aortic arch, left atrium, etc.) may be used to determine or to update an optimal delay. Further, information may be collected over a period of time to determine heart condition (e.g., deterioration, improvement, etc.).

Various exemplary methods, devices, systems, etc., optionally rely on interference between an intrinsic stimulus and a non-intrinsic stimulus or between two non-intrinsic stimuli. A common form of interference is known as "fusion". While various aforementioned examples may aim to avoid fusion, other examples deliberately seek the occurrence of fusion (i.e., intentional fusion).

An exemplary method may alternate between a normally timed pacing stimulus and one aimed at causing fusion. According to such a method, if the normally timed pacing stimulus does not cause an evoked response, then the capture threshold may have changed. Under such circumstances, the "fusion" test should be halted until capture is ensured. Alternatively, a fusion test may use a high energy level (e.g., back-up level or other elevated level).

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method of determining an advance atrio-ventricular pacing interval (AV advance or PV advance) for use in place of an AV/PV interval for pacing a ventricle of a heart with a slower atrio-ventricular conduction relative to a ventricle with a faster atrio-ventricular conduction, said method comprising:
   providing an optimal interventricular interval (VVOpt);
   extending the AV/PV interval and while the AV/PV interval is extended, determining an atrio-ventricular conduction delay (AR or PR) for the ventricle having faster atrio-ventricular conduction, wherein the delay is a measure of time between an atrial event, either paced or intrinsic, and an intrinsic event in the ventricle having faster atrio-ventricular conduction;
   shortening the AV/PV interval and while the AV/PV interval is shortened, determining an interventricular conduction delay (IVCD), wherein the delay is a measure of time between a paced event in the ventricle having slower atrio-ventricular conduction and an intrinsic event in the ventricle having faster atrio-ventricular conduction; and
   determining an advance atrio-ventricular pacing interval (AV advance or PV advance), for use in pacing the ventricle having slower atrio-ventricular conduction, based at least in part on the optimal interventricular interval (VVOpt) and the interventricular conduction delay (IVCD).

2. The method of claim 1 wherein delivery of stimulation to the ventricle having slower atrio-ventricular conduction, according to the advance atrio-ventricular pacing interval (AV advance or PV advance), fuses with depolarization of the ventricle having faster atrio-ventricular conduction.

3. The method of claim 2 wherein the fusion occurs at the interventricular septum.

4. The method of claim 1 wherein determining an advance atrio-ventricular pacing interval comprises determining a correction factor (CVV) based on the optimal interventricular interval (VVOpt) and the interventricular conduction delay (IVCD).

5. The method of claim 1 wherein determining an atrio-ventricular conduction delay for the ventricle having faster atrio-ventricular conduction comprises determining if at least some degree of bundle branch block exists for a ventricle.

6. The method of claim 1 wherein providing comprises providing an optimal interventricular interval (VVOpt) determined using echocardiography data.

7. The method of claim 1 wherein determining an interventricular conduction delay (IVCD) comprises pacing the ventricle having slower atrio-ventricular conduction time and detecting a conducted evoked response in the other ventricle.

8. The method of claim 1 further comprising delivering stimulation to the ventricle having slower atrio-ventricular conduction according to the advance atrio-ventricular pacing interval (AV advance or PV advance).

9. The method of claim 8 further comprising sensing cardiac activity after delivering stimulation to the ventricle having slower atrio-ventricular conduction.

10. The method of claim 9 further comprising calling for delivery of stimulation to the ventricle having faster conduction if the sensing does not detect cardiac activity in that ventricle.

11. The method of claim 1 further comprising sensing cardiac activity prior to deliver of stimulation to the ventricle having slower atrio-ventricular conduction.

12. The method of claim 11 further comprising preventing delivery of stimulation to the ventricle having slower conduction if the sensing detects cardiac activity in that ventricle.

13. The method of claim 1 further comprising comparing the advance atrio-ventricular pacing interval (AV advance or PV advance) to a limit.

14. The method of claim 1 further comprising comparing the advance atrio-ventricular pacing interval (AV advance or PV advance) to one or more previously determined in advance atrio-ventricular pacing intervals.

15. The method of claim 1 further comprising re-determining the advance atrio-ventricular pacing interval (AV advance or PV advance) responsive to a change in heart rate.

16. The method of claim 1 further comprising re-determining the advance atrio-ventricular pacing interval (AV advance or PV advance) responsive to a change in atrio-ventricular conduction delay.

17. The method of claim 4 wherein the correction factor is determined using the equation: $CVV = (IVCD - VVOpt)/IVCD$.

18. The method of claim 4 wherein the advance atrio-ventricular pacing interval is determined using the equation: $PV/AV\ advance = (PV/AV\ interval) - (IVCD) \times (1 - CVV)$.

* * * * *